United States Patent
Fujimoto

(10) Patent No.: US 8,079,952 B2
(45) Date of Patent: Dec. 20, 2011

(54) ENDOSCOPE CLEANING SHEATH, AND ENDOSCOPE APPARATUS AND ENDOSCOPE COMPRISING THE CLEANING SHEATH

(75) Inventor: Ryuhei Fujimoto, Tokyo (JP)

(73) Assignee: Olympus Medical Systems Corp, Tokyo (JP)

(*) Notice: Subject to any disclaimer, the term of this patent is extended or adjusted under 35 U.S.C. 154(b) by 1110 days.

(21) Appl. No.: 11/973,230

(22) Filed: Oct. 5, 2007

(65) Prior Publication Data

US 2008/0188715 A1 Aug. 7, 2008

(30) Foreign Application Priority Data

Oct. 11, 2006 (JP) .................................. 2006-278041

(51) Int. Cl.
*A61B 1/12* (2006.01)

(52) U.S. Cl. ........ 600/157; 600/121; 600/123; 600/155; 600/156; 600/158

(58) Field of Classification Search .......... 600/121–125, 600/153–159
See application file for complete search history.

(56) References Cited

U.S. PATENT DOCUMENTS

| | | | |
|---|---|---|---|
| 4,991,565 A * | 2/1991 | Takahashi et al. ............ | 600/123 |
| 5,386,817 A * | 2/1995 | Jones ............................ | 600/104 |
| 5,408,991 A * | 4/1995 | Iida et al. ...................... | 600/133 |
| 5,431,150 A * | 7/1995 | Yabe et al. ..................... | 600/121 |
| 5,575,756 A * | 11/1996 | Karasawa et al. ............. | 600/157 |
| 5,630,782 A * | 5/1997 | Adair ............................ | 600/133 |
| 5,725,477 A * | 3/1998 | Yasui et al. .................... | 600/127 |
| 5,733,243 A * | 3/1998 | Yabe et al. ..................... | 600/121 |
| 5,827,177 A * | 10/1998 | Oneda et al. ................... | 600/121 |
| 6,126,592 A | 10/2000 | Proch et al. | |
| 6,409,657 B1 * | 6/2002 | Kawano ......................... | 600/157 |
| 6,620,096 B2 * | 9/2003 | Arai et al. ...................... | 600/156 |
| 7,056,284 B2 * | 6/2006 | Martone et al. ............... | 600/123 |
| 7,435,214 B2 * | 10/2008 | Kucklick et al. .............. | 600/125 |

FOREIGN PATENT DOCUMENTS

| | | |
|---|---|---|
| JP | 63-49502 | 10/1988 |
| JP | 2004-141367 | 5/2004 |
| JP | 2004-267583 | 9/2004 |

* cited by examiner

*Primary Examiner* — Matthew J Kasztejna

(74) *Attorney, Agent, or Firm* — Scully, Scott, Murphy & Presser, P.C.

(57) ABSTRACT

An endoscope cleaning sheath includes a tube body and a distal end configuration portion. The tube body includes an endoscope disposition hole in which an insertion portion of an endoscope provided with at least an observation window is inserted and disposed, at least one liquid supply hole configuring a liquid supply channel, and at least one gas supply hole configuring a gas supply channel. The distal end configuration portion is fixed to a distal end portion of the tube body. On an inner surface of a distal end surface portion of the distal end configuration portion is provided a fluid mixing portion and a concave portion configuring an ejection opening that ejects a fluid mixture at an observation window of the endoscope. The fluid mixing portion causes liquid supplied through the liquid supply hole and gas supplied through the gas supply hole to merge to mix the liquid and gas.

4 Claims, 17 Drawing Sheets

ENDOSCOPE CLEANING SHEATH, AND ENDOSCOPE APPARATUS AND ENDOSCOPE COMPRISING THE CLEANING SHEATH

This Application claims benefit of Japanese Application No. 2006-278041 filed in Japan on Oct. 11, 2006, the contents of which are incorporated by this reference.

BACKGROUND OF THE INVENTION

1. Field of the Invention

The present invention relates to an endoscope cleaning sheath that sprays a fluid mixture in a spray state towards an observation window or the like of an endoscope to remove an adhering substance that is adhered to the observation window or the like, as well as an endoscope apparatus comprising the cleaning sheath.

2. Description of the Related Art

When in vivo mucus, blood, fat, dirt or the like adhere to an observation window, illumination window or the like comprised by an endoscope during observation using the endoscope, favorable observation is prevented.

Japanese Patent Laid-Open No. 2004-267583 (hereunder, referred to as Patent Document 1), for example, discloses a laparoscope defogging apparatus to solve the problems caused by such adherence. A laparoscope defogging apparatus is a separate device to a laparoscope, and is attached to a laparoscope to prevent fogging and the like of a distal end portion of the laparoscope. The laparoscope defogging apparatus illustrated in FIG. 4 of Patent Document 1 has a cylindrical body 3. The cylindrical body 3 has an opening 30 at the proximal end and an opening 31 at the distal end thereof. An optical transmission member 4 that has a hydrophilic coating formed thereon is provided on the side of the opening 31 of the cylindrical body 3. A main unit 1 of the laparoscope can be inserted from the opening 30 at the proximal end of the cylindrical body 3. The cylindrical body 3 comprises a light guide 35 for irradiating light from the distal end and a moisture supply hole 37 for supplying moisture. Accordingly, by supplying moisture to the optical transmission member 4 on which the hydrophilic coating is formed through the moisture supply hole 37 on the coating surface of the optical transmission member 4, the surface of the optical transmission member undergoes self cleaning.

In the above described laparoscope defogging apparatus, prevention of fogging that occurs on the surface of the optical transmission member 4 is effective in a case in which dirt such as blood is adhered in a very small quantity on the surface. However, once dirt such as blood has adhered to the surface of the optical transmission member 4, it is difficult to remove the adhering substance.

It is already known that spraying a fluid mixture of water and air in a spray state towards the external surface of an observation window from a spray nozzle produces a better cleaning effect than a case of spraying only water onto the surface of an observation window. Further, Japanese Patent Publication No. 63-49502 (hereunder, referred to as Patent Document 2) discloses an endoscope in which means that cleans an outer surface of an observation window is improved. Furthermore, Japanese Patent Laid-Open No. 2004-141367 (hereunder, referred to as Patent Document 3) discloses a water pipeline for an endoscope that ejects a fluid mixture of water and air in a spray state from the distal end of an insertion portion without swelling a patient's body cavity employing a simple configuration.

On an endoscope main unit 1 shown in FIG. 1 of Patent Document 2, a switching valve 16 is provided in an operation portion 2. Supply of a fluid mixture of a cleaning liquid and a gas and supply of only air can be selectively performed to a spray nozzle 6 when a supply hole 11 comprising an air supply channel 12 and a liquid supply channel 13 is switched by a changeover operation of the switching valve 16. The switching valve 16 is configured by inserting a piston 18 into a cylinder 17, and a throttle 29 that suppresses the amount of fed air when supplying a fluid mixture is formed as suppression means in the piston 18. As shown in FIG. 2 of Patent Document 2, when cleaning an observation window 5, a leak hole 27 of the piston 18 is blocked with a finger and the piston 18 is inserted. Subsequently, feeding of air that passes through the air supply channel 12 and feeding of liquid that passes through the liquid supply channel 13 are performed at the same time to mix the cleaning liquid and gas at a position immediately before the spray nozzle 6. By mixing the cleaning liquid and gas at a position immediately before the spray nozzle 6, a fluid mixture is sprayed in a spray state towards an observation window 5 from the spray nozzle 6 to remove dirt that is adhered to the surface of the observation window 5.

Accordingly, it is considered that dirt adhering to the optical transmission member 4 will be removed by supplying a fluid mixture to the moisture supply hole 37 of the laparoscope defogging apparatus, more specifically, by supplying a fluid mixture from a water supply hole 36.

A fluid ejection opening 6 aligned with an observation window 3 is formed on a distal end surface of a distal end portion main unit 2 of an insertion portion 1 illustrated in FIG. 1 of Patent Document 3. A water supply channel 7 is formed at the rear of the distal end portion main unit 2. A narrowed portion 7a that locally narrows the cross sectional area of the flow channel is formed at a portion towards the tip of the water supply channel 7. A distal end portion from the narrowed portion 7a to the fluid ejection opening 6 is formed in a shape that widens in a trumpet shape. A ventilation path 9 is formed in the distal end portion main unit 2. One end of the ventilation path 9a opens on a lateral wall surface near the outlet of the narrowed portion 7a of the water supply channel 7, and the other end opens towards the external surface on the distal end surface of the distal end portion main unit 2. According to this configuration, when water is fed to the water supply channel 7 through a water supply tube 8 and the water passes through the narrowed portion 7a, the flow rate of the water flow at that portion quickens and the pressure decreases. Thereupon, air in the area surrounding the distal end portion main unit 2 is sucked into the narrowed portion 7a through the ventilation path 9 and, as a result, a fluid mixture of water and air is ejected from the fluid ejection opening 6.

SUMMARY OF THE INVENTION

An endoscope cleaning sheath comprises a tube body and a distal end configuration portion. The tube body includes an endoscope disposition hole and at least one liquid supply hole and one gas supply hole. An elongated insertion portion of an endoscope provided with at least an observation window on a distal end surface of the insertion portion is disposed in the endoscope disposition hole. The liquid supply hole configures a liquid supply channel that supplies a liquid such as water. The gas supply hole configures a gas supply channel that supplies a gas such as air. The distal end configuration portion is a cylindrical body that is provided in a fixed condition at the distal end portion of the tube body. The cylindrical body includes a notch portion that places in an exposure state an observation window that is provided on a distal end surface of the endoscope that is disposed in the endoscope disposition hole. An inner surface of a distal end surface portion of the distal end configuration portion has, in a state in which a distal end surface of the tube body and the distal end surface of the insertion portion are in a contacting state at a contact surface at which a part of the distal end surface and a part of a distal end surface of the insertion portion of the endoscope come in contact, a fluid mixing portion and a concave portion configuring an ejection opening. The fluid mixing portion mixes a liquid and a gas by causing a liquid that is supplied through the liquid supply hole and a gas that is supplied through the gas supply hole to merge. The ejection opening ejects a fluid mixture that is mixed at the fluid mixing portion at an observation window of the endoscope.

The above and other objects, features and advantages of the invention will become more clearly understood from the following description referring to the accompanying drawings.

BRIEF DESCRIPTION OF THE DRAWINGS

FIG. 1 is a view that illustrates an endoscope comprising an endoscope apparatus and an endoscope cleaning sheath that is integrally disposed on an insertion portion of the endoscope;

FIG. 2 is a cross section that illustrates the configuration of principle portions of the endoscope cleaning sheath that is integrally disposed on the insertion portion of the endoscope;

FIG. 3 is a longitudinal section along a line III-III shown in FIG. 2 that illustrates a tube body comprising the endoscope cleaning sheath;

FIG. 4 is a view that describes the relation between the endoscope cleaning sheath comprising the endoscope apparatus and an air supply apparatus and a liquid supply apparatus;

FIG. 5 is a front elevation view of a distal end configuration portion comprising the endoscope cleaning sheath;

FIG. 6 is a rear elevation view of the distal end configuration portion shown in FIG. 5;

FIG. 7 is a view that illustrates the action of a concave portion that is formed in a contact surface of the distal end configuration portion;

FIG. 8 is a view that illustrates the action of the endoscope apparatus, and shows a state in which a fluid mixture is being ejected from an ejection opening towards the center direction of an observation window of the endoscope; and FIG. 9 is a view showing the state when a fluid merging portion comprising a concave portion is viewed from the direction of an arrow B shown in FIG. 6.

FIG. 10 is a view that illustrates an endoscope apparatus comprising an ejection state changeover switch;

FIG. 11 is a view that illustrates a configuration example of the ejection state changeover switch;

FIG. 12 is a front schematic view that illustrates the state of an air supply regulation member and a liquid supply regulation member in an ejection stopped state that is the initial state of the ejection state changeover switch;

FIG. 13 is a front schematic view that illustrates the state of the air supply regulation member and the liquid supply regulation member when the ejection state changeover switch is in an ejection state;

FIG. 14 is a view showing a center ejection state in which a fluid mixture is ejected from the ejection opening towards the center of an observation window of the endoscope;

FIG. 15 is a front schematic view that illustrates the state of the air supply regulation member and the liquid supply regulation member when the ejection state changeover switch is in a one-side ejection state;

FIG. 16 is a view showing a one-side ejection state in which the fluid mixture is ejected from the ejection opening towards one side of the observation window of the endoscope;

FIG. 17 is a front schematic view illustrating a state of the air supply regulation member and the liquid supply regulation member when the ejection state changeover switch is in an other-side ejection state;

FIG. 18 is a view showing the other-side ejection state in which a fluid mixture is ejected from the ejection opening towards the other side of the observation window of the endoscope;

FIG. 21 is a view that illustrates the configuration of an ejection state changeover switch comprising a switch portion that is slidingly movable;

FIG. 22 is a front elevation that illustrates the configuration of the ejection state changeover switch;

FIG. 23 is a schematic view that illustrates the state of an air supply regulation member and a liquid supply regulation member in an ejection stopped state that is the initial state of the ejection state changeover switch;

FIG. 24 is a front schematic view that illustrates the state of the air supply regulation member and the liquid supply regulation member when the ejection state changeover switch is in a center ejection state;

FIG. 25 is a front schematic view showing a state in which the switch portion is slid to one side to place the ejection state changeover switch in a one-side ejection state;

FIG. 26 is a top view that illustrates a state of the air supply regulation member and the liquid supply regulation member in the one-side ejection state shown in FIG. 25; and FIG. 27 is a front schematic view of an air supply state in which the switch portion of the ejection state changeover switch is slidably moved further to one side from the one-side ejection state shown in FIG. 26.

FIG. 28 is a view that illustrates an endoscope apparatus comprising an ejection state changeover switch;

FIG. 29 is a front elevation that illustrates the configuration of an ejection state changeover switch comprising two air supply regulation members and one liquid supply regulation member;

FIG. 30 is a front schematic view that illustrates the state of the air supply regulation members and the liquid supply regulation member in an ejection stopped state that is the initial state of the ejection state changeover switch;

FIG. 31 is a front schematic view that illustrates the state of the air supply regulation members and the liquid supply regulation member in an air supply state in which a switch portion of the ejection state changeover switch is pushed in a predetermined amount;

FIG. 32 is a front schematic view that illustrates the state of the air supply regulation members and the liquid supply regulation member in an ejection state in which the switch portion of the ejection state changeover switch is pushed in further;

FIG. 33 is a view showing a state in which a fluid mixture is ejected in a center ejection state from an ejection opening to an observation window of the endoscope;

FIG. 34 is a front schematic view that illustrates the state of the air supply regulation members and the liquid supply regulation member when the ejection state changeover switch is in a one-side ejection state;

FIG. 35 is a view showing a one-side ejection state in which the fluid mixture is ejected from the ejection opening towards one side of the observation window of the endoscope;

FIG. 36 is a front schematic view illustrating a state of the air supply regulation members and the liquid supply regulation member when the ejection state changeover switch is in an other-side ejection state;

FIG. 37 is a view showing an other-side ejection state in which a fluid mixture is ejected from the ejection opening towards the other side of the observation window of the endoscope;

DETAILED DESCRIPTION OF THE PREFERRED EMBODIMENTS

Hereunder, the embodiments of the present invention are described with reference to the attached drawings.

A first embodiment of the endoscope apparatus comprising the endoscope cleaning sheath of the present invention will be described referring to FIG. 1 to FIG. 9.

Figure 1:
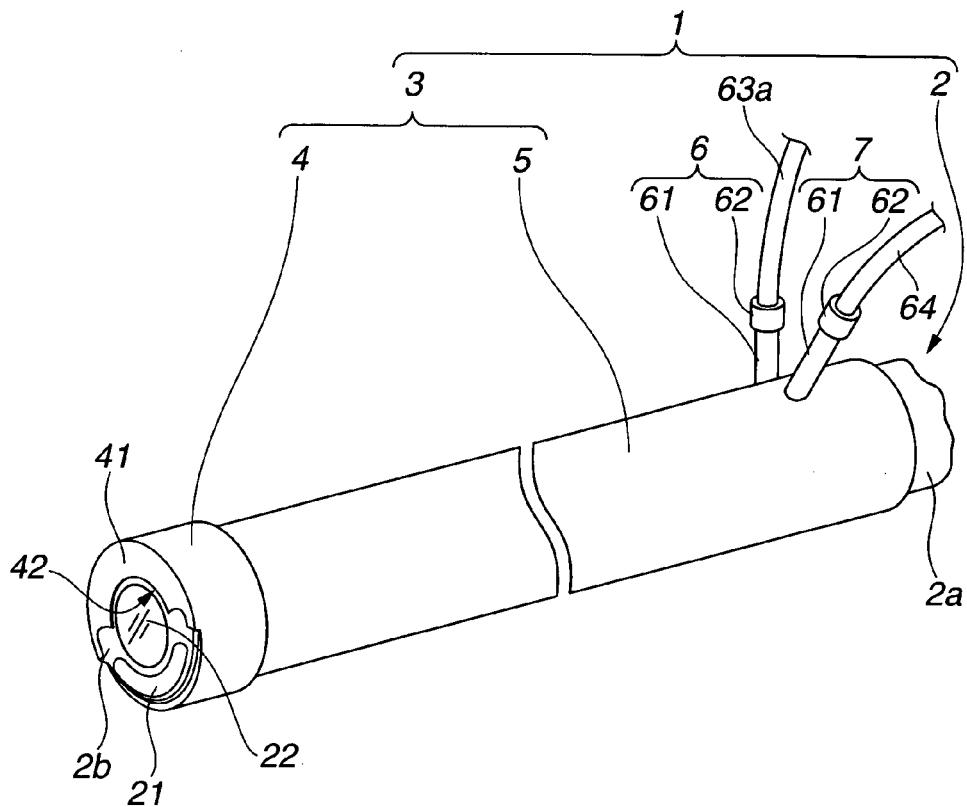
FIG. 1 to FIG. 9 are views illustrating a first embodiment of an endoscope apparatus comprising an endoscope cleaning sheath according to the present invention.

As shown in FIG. 1, an endoscope apparatus 1 principally comprises an endoscope 2, an endoscope cleaning sheath 3, an air supply apparatus 60 that is described later, and a liquid supply apparatus 70 that is described later. The endoscope cleaning sheath 3 is attached to an insertion portion 2a of the endoscope 2, and is inserted into a body cavity in a manner in which it is integrated with the insertion portion 2a.

In the endoscope 2, for example, the insertion portion 2a is a flexible and slender flexible mirror. At a distal end surface 2b of the insertion portion 2a are provided a light emitting end 21 of a light guide comprising an illumination optical system and an observation window 22 comprising an observation optical system.

The light incident end of the light guide is connected to an unshown light source. The observation optical system comprises an image pickup apparatus comprising, for example, an image pickup device such as a CCD that subjects an optical image that is picked up through the observation window 22 to photoelectric conversion into an electrical signal. A signal cable extends from the image pickup apparatus. The signal cable is connected to an unshown camera control unit.

Thus, reflection light from a subject that is illuminated by illumination light that is emitted from the light emitting end 21 is picked up as an optical image through the observation window 22. The optical image is converted into an electrical signal at the image pickup device, and the electrical signal is then sent to the camera control unit. At the camera control unit, after generating a video signal from the electrical signal, the video signal is outputted to an unshown, for example, liquid crystal display as a display apparatus, to display the endoscopic image on the screen of the liquid crystal display.

The endoscope cleaning sheath 3 is formed as a slender cylindrical member and is disposed so as to cover the insertion portion 2a of the endoscope 2. The endoscope cleaning sheath 3 is principally comprised by, in order from the distal end side, a distal end configuration portion 4 that is a cylindrical body, and a tube body 5 comprising a multi-lumen tube. The distal end configuration portion 4 is fixed to a distal end portion of the tube body 5. The tube body 5 comprises, for example, on a side portion of a proximal end side thereof, a gas supply portion 6 and a liquid supply portion 7. Reference numeral 63a denotes a first air supply tube that comprises a fluid channel of the air supply apparatus 60 that is described later. Reference numeral 64 denotes a liquid supply tube that comprises a fluid channel of the liquid supply apparatus 70 that is described later. The multi-lumen tube is formed with a flexible material such as silicon, urethane, or Teflon (registered trademark), or a hard material such as polyamide, polyethylene, polypropylene, or polycarbonate.

Figure 2:
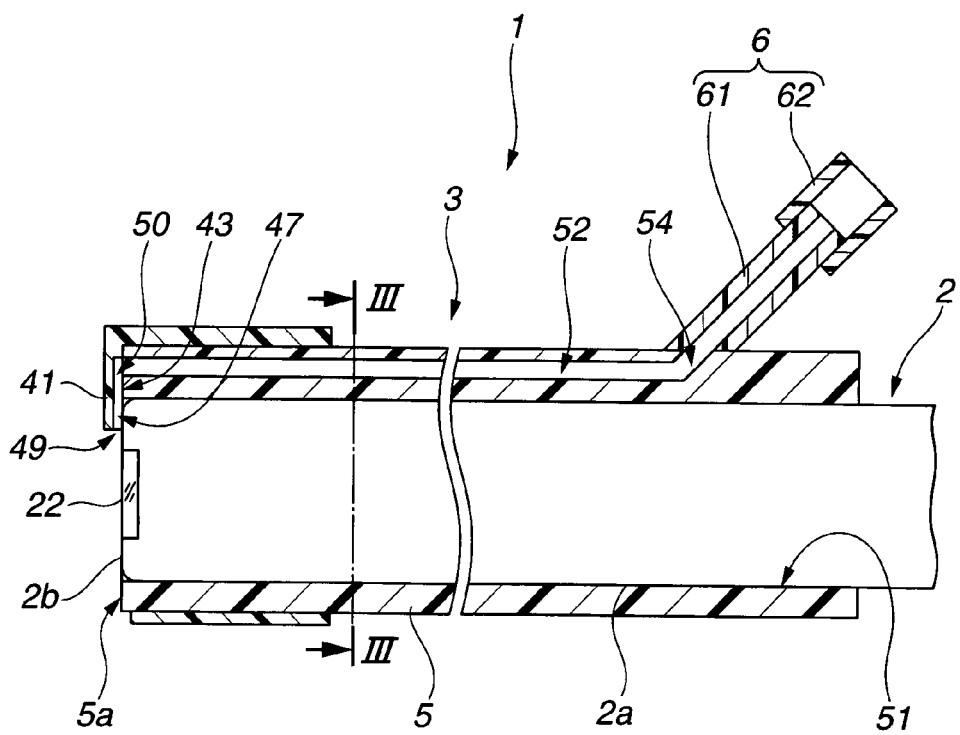
Figure 3:
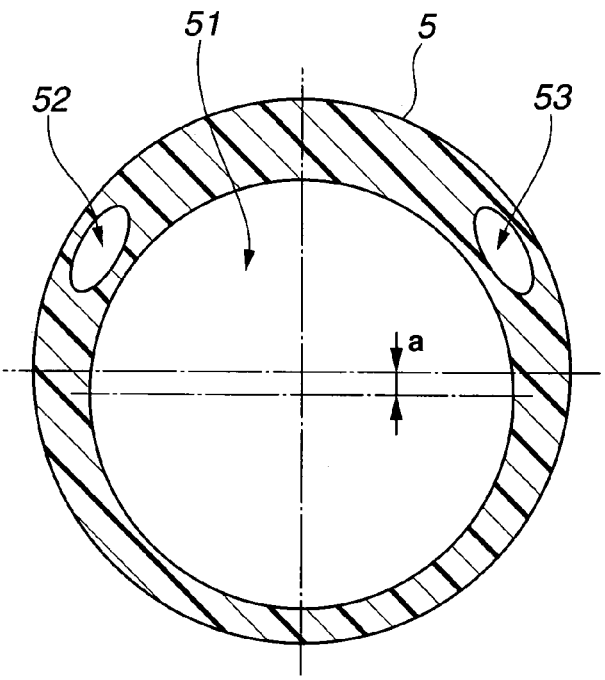

As shown in FIG. 2 and FIG. 3, the tube body 5 comprises, for example, three holes 51, 52, and 53. The hole 51 is an endoscope disposition hole (hereunder, abbreviated as "endoscope hole"), and is a through-hole having openings in the proximal end surface and distal end surface of the tube body 5. The insertion portion 2a of the endoscope 2 is inserted inside the endoscope hole 51. The central axis of the tube body 5 and the central axis of the endoscope hole 51 are parallel with respect to the horizontal direction, and are eccentric in the downward direction on the vertical axis shown in FIG. 3 by a previously set distance a. Accordingly, the thickness dimensions of the tube body 5 are not uniform, and the tube body 5 has a non-uniform structure in which the upper side in the figure has a thick wall and the lower side in the figure has a thin wall.

The hole 52 is a gas supply hole (hereunder, abbreviated as "air supply hole") 52 comprising a gas supply channel for supplying a gas such as air. The hole 52 is formed at a predetermined position in the thick-walled portion side of the tube body 5. A distal end side opening of the air supply hole 52 is formed in the distal end surface of the tube body 5, and a proximal end side opening thereof is formed in the side surface of the proximal end side of the tube body 5.

The hole 53 is a liquid supply hole 53 comprising a liquid supply channel for supplying a liquid such as water or a cleaning liquid (hereunder, abbreviated as "liquid supply hole"). The hole 53 is formed at a predetermined position in the thick-walled portion side of the tube body 5. A distal end side opening of the liquid supply hole 53 is formed in the distal end surface of the tube body 5, and a proximal end side opening thereof is formed in the side surface of the proximal end side of the tube body 5.

The holes 52 and 53 have substantially the same shape and substantially the same cross-sectional area. The holes 52 and 53 are formed in a symmetrical positional relationship in a manner that sandwiches the aforementioned vertical axis. The hole 52 and hole 53 are fluid holes for supplying a fluid such as a liquid or a gas. A configuration may also be adopted in which the hole 52 is a liquid supply hole and the hole 53 is an air supply hole.

The openings on the proximal end side of the holes 52 and 53 are openings of a communicating hole 54 that is formed so as to communicate to the respective holes 52 and 53 from a side surface on the proximal end side of the tube body 5. The tube body 5 is a multi-lumen tube. Therefore, the original proximal end side openings of the holes 52 and 53 are formed in the proximal end surface of the tube body 5. The proximal end side openings of the respective holes 52 and 53 are previously blocked up by hot welding. Alternatively, the proximal end side openings are blocked by filling the openings with an unshown blocking member from the proximal end side opening.

As shown in FIG. 1 and FIG. 2, the gas supply portion 6 and the liquid supply portion 7 are provided in a manner in which they protrude from the side surface on the proximal end side of the tube body 5. The gas supply portion 6 and the liquid supply portion 7 are, for example, formed by coupling together a first pipe member 61 and a second pipe member 62. According to the present embodiment, the second pipe member 62 has a larger diameter than the first pipe member 61.

The first pipe member 61 is a supply portion main unit that is disposed in communication with the communicating hole 54. In contrast, the second pipe member 62 is an attachment portion that is attached to a distal end portion of a fluid tube such as the first air supply tube 63a or a liquid supply tube 64. The outer circumferential surface of the distal end portion of the fluid tube is disposed on, for example, the inner circumferential surface side of the second pipe member 62.

The gas supply portion 6 and the liquid supply portion 7 may be comprised by a single pipe member comprising a small-diameter portion and a large diameter portion, or a pipe member whose outer diameter dimensions do not change. Further, a configuration may be adopted in which a fluid tube is attached to the outer circumferential surface side of a pipe member comprising the gas supply portion 6 and the liquid supply portion 7.

The air supply apparatus 60 that supplies air to the gas supply portion 6 and the liquid supply apparatus 70 that supplies, for example, water to the liquid supply portion 7 will now be described with reference to FIG. 4.

Figure 4:
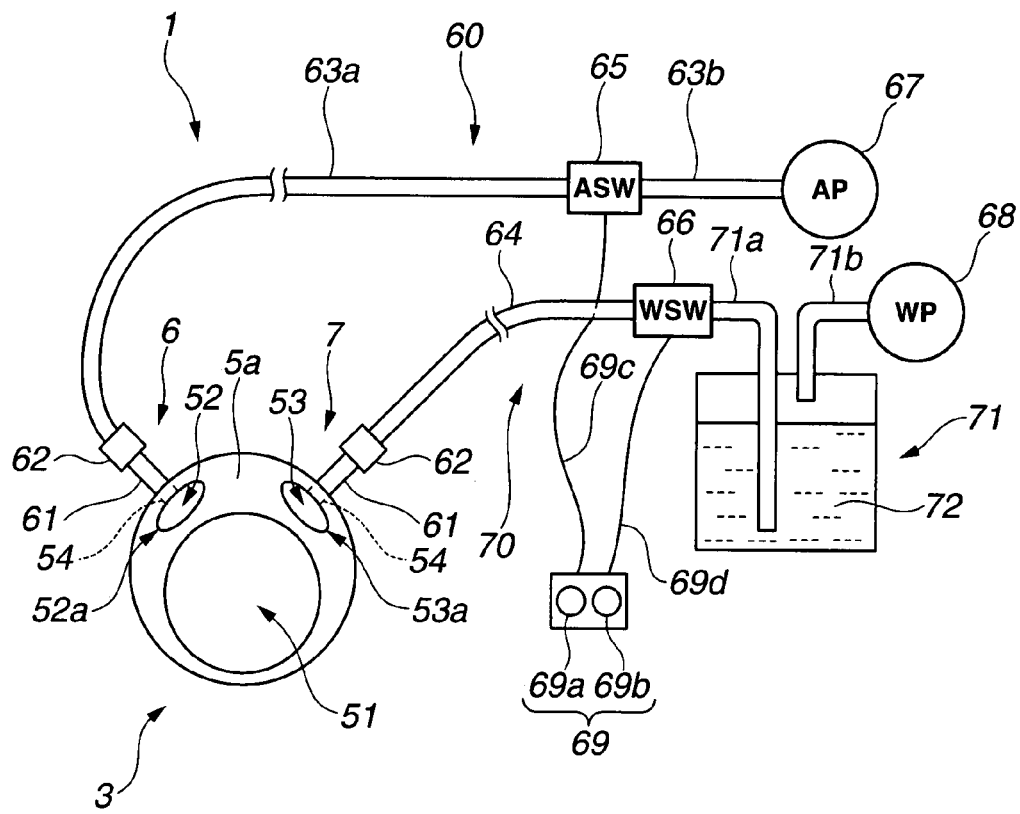
Figure 5:
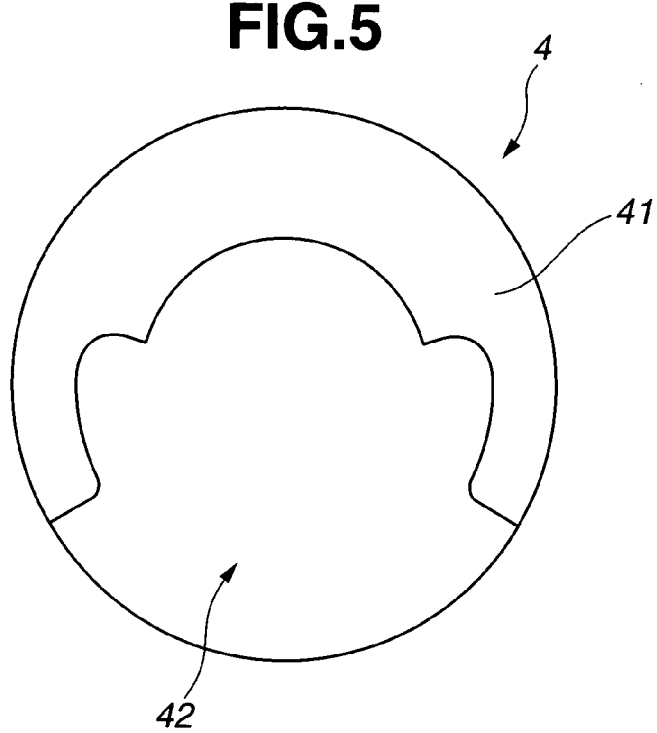
Figure 6:
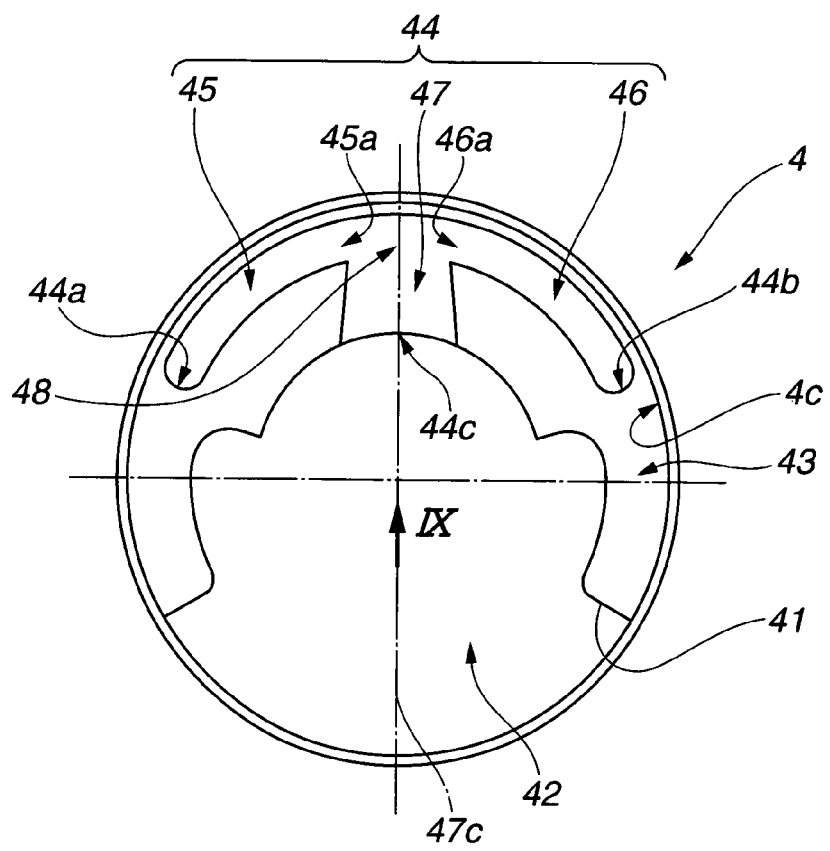

As shown in FIG. 4, one end of the first air supply tube 63a is, for example, detachably attached to the second pipe member 62 comprising the gas supply portion 6. Further, one end of the liquid supply tube 64 is, for example, detachably attached to the second pipe member 62 comprising the liquid supply portion 7.

The other end of the first air supply tube 63a is connected to an air supply control switch 65 having an unshown open/close valve as a control apparatus. One end of a second air supply tube 63b comprising a fluid channel is connected to the air supply control switch 65. The other end of the second air supply tube 63b is connected to an air supply pump 67. That is, the air supply apparatus 60 is constituted including the air supply pump 67, the air supply tubes 63a and 63b, and the air supply control switch 65.

Meanwhile, the other end of the liquid supply tube 64 is connected to a liquid supply control switch 66 having an unshown open/close valve as a control apparatus. One end of a liquid supply pipe 71a that is a fluid channel provided to a liquid supply tank 71 is connected to the liquid supply control switch 66. In addition to the liquid supply pipe 71a, the liquid supply tank 71 comprises a pressurized pipe 71b. One end of the pressurized pipe 71b is connected to a liquid supply pump 68. For example, water 72 is stored inside the liquid supply tank 71. The other end of the liquid supply pipe 71a is disposed in a submerged state close to the bottom surface of the liquid supply tank 71. The other end of the pressurized pipe 71b is disposed in a state in which it is positioned above the surface of the water in the liquid supply tank 71. More specifically, the liquid supply apparatus 70 is constituted including the liquid supply tank 71 comprising the liquid supply pump 68 and the pipes 71a and 71b, the liquid supply control switch 66, and the liquid supply tube 64.

Reference numeral 69 denotes a foot switch as instructing means that comprises, for example, a first pedal 69a and a second pedal 69b. The first pedal 69a, for example, outputs an instruction signal to place both a valve of the air supply control switch 65 and a valve of the liquid supply control switch 66 in an open state. The second pedal 69b, for example, outputs an instruction signal to place both a valve of the air supply control switch 65 and a valve of the liquid supply control switch 66 in a closed state.

Therefore, when the air supply pump 67 and the liquid supply pump 68 are in an operating state, the user places both a valve of the air supply control switch 65 and a valve of the liquid supply control switch 66 in an open state by operating the first pedal 69a of the foot switch 69. Thus, air that is fed through the second air supply tube 63b from the air supply pump 67 is supplied to the first air supply tube 63a by passing through the air supply control switch 65.

In this case, when the distal end portion of the first air supply tube 63a is attached to the second pipe member 62 comprising the gas supply portion 6, air that is supplied to the first air supply tube 63a is ejected from an air supply distal end opening 52a after passing through the first pipe member 61, the communicating hole 54, and the air supply hole 52. That is, the air supply apparatus 60 comprises a gas supply channel comprised by the second air supply tube 63b, the air supply control switch 65 with the valve in an open state, and the first air supply tube 63a.

On the other hand, the water 72 inside the liquid supply tank 71 is pressurized by air that is supplied through the pressurized pipe 71b from the liquid supply pump 68 and supplied through the liquid supply pipe 71a and the liquid supply control switch 66 to the liquid supply tube 64. In this case, when the distal end portion of the liquid supply tube 64 is attached to the second pipe member 62 comprising the liquid supply portion 7, the water 72 supplied to the liquid supply tube 64 passes through the first pipe member 61, the communicating hole 54, and the liquid supply hole 53 to be ejected from a liquid supply distal end opening 53a. That is, the liquid supply apparatus 70 comprises a fluid supply channel comprised by the liquid supply pipe 71a, the liquid supply control switch 66 with the valve in an open state, and the liquid supply tube 64.

The configuration of the distal end configuration portion 4 will now be described.

The distal end configuration portion 4 is formed, for example, with a resin member that is rigid and transparent or semi-transparent. The distal end configuration portion 4 is integrally provided in a fixed condition at the distal end portion of the tube body 5 to comprise the endoscope cleaning sheath 3.

As shown in FIG. 1, FIG. 2, FIG. 5, and FIG. 6, a notch portion 42 for placing the aforementioned light emitting end 21 and observation window 22 in an exposure state is formed in a distal end surface portion 41 that is the distal end surface of the distal end configuration portion 4. An inner surface of the distal end surface portion 41 that is the bottom face of the distal end configuration portion 4 is a contact surface 43. At the contact surface 43, a part of a distal end surface 5a of the tube body 5 and a part of a distal end surface 2b of the insertion portion 2a contact against each other. A T-shaped groove 44 comprised by a substantially T-shaped concave portion is formed in the contact surface 43. The T-shaped groove 44 comprises two blocked ends 44a and 44b and one open end 44c.

The T-shaped groove 44 includes a liquid supply groove 45 comprising a liquid supply channel that is a fluid channel, a gas supply groove (hereunder, referred to as "air supply groove") 46 that comprises a gas supply channel that is a fluid channel, and a fluid mixture supply groove (hereunder, referred to as "ejection groove") 47 that comprises a fluid mixture supply channel. The liquid supply groove 45 is formed along an inner circumferential surface 4*c* and comprises the blocked end 44*a*. The air supply groove 46 is formed along the inner circumferential surface 4*c* and comprises the blocked end 44*b*. The ejection groove 47 constitutes an ejection opening and comprises the open end 44*c*.

An open end 45*a* on the other end side of the liquid supply groove 45 and an open end 46*a* on the other end side of the air supply groove 46 are provided in a condition facing each other at a clearance of a predetermined distance to constitute a spatial portion at which liquid and gas flow together. This spatial portion is the fluid merging portion 48 that comprises a fluid mixing portion 50 at which a liquid and a gas merge to obtain a fluid mixture. The ejection groove 47 extends from the fluid merging portion 48 towards the notch portion 42. More specifically, a center line 47*c* of the ejection groove 47 extends from the center of the fluid merging portion 48 so as to be orthogonal to the central axis of the distal end configuration portion 4. Note that, according to the present embodiment, the groove width of the ejection groove 47 is designed so as to gradually widen in the direction from the fluid merging portion 48 towards the open end 44*c*.

The position of the blocked end 44*a* of the liquid supply groove 45 is set while taking into account the position of the liquid supply distal end opening 53*a* of the liquid supply hole 53 that is formed in the tube body 5. More specifically, in a state in which the distal end configuration portion 4 is provided in a condition in which it is integrally fixed to the distal end portion of the tube body 5, the liquid supply distal end opening 53*a* is disposed facing the blocked end 44*a* side of the liquid supply groove 45. Thus, liquid ejected from the liquid supply distal end opening 53*a* is supplied to the liquid supply groove 45.

Similarly to the liquid supply groove 45, the position of the blocked end 44*b* of the air supply groove 46 is set while taking into account the position of the air supply distal end opening 52*a* of the air supply hole 52 that is formed in the tube body 5. More specifically, in a state in which the distal end configuration portion 4 is provided in a condition in which it is integrally fixed to the distal end portion of the tube body 5, the air supply distal end opening 52*a* is disposed facing the blocked end 44*b* side of the air supply-groove 46. Thus, gas ejected from the air supply distal end opening 52*a* is supplied to the air supply groove 46.

In a state in which a part of the distal end surface of the tube body 5 contacts against the contact surface 43 of the distal end configuration portion 4, the liquid supply groove 45 is configured as a liquid supply channel that supplies liquid that is supplied through the liquid supply hole 53 of the tube body 5 to the fluid merging portion 48. Meanwhile, in a state in which a part of the distal end surface of the tube body 5 contacts against the contact surface 43 of the distal end configuration portion 4, the air supply groove 46 is configured as a gas supply channel that supplies gas that is supplied through the air supply hole 52 of the tube body 5 to the fluid merging portion 48. The fluid merging portion 48 is configured as the fluid mixing portion 50 in which a fluid mixture is obtained, and the ejection groove 47 is configured as a fluid mixture supply channel that supplies a fluid mixture.

In this connection, the open end 44*c* is configured as an ejection opening 49 in a state in which that distal end surface of the tube body 5 and the distal end surface 2*b* of the insertion portion 2*a* substantially contact with the contact surface 43 of the distal end configuration portion 4. When a fluid mixture that is mixed at the fluid mixing portion 50 is supplied to the ejection opening 49 through the ejection groove 47, the fluid mixture is ejected towards the observation window 22 of the endoscope 2 from the ejection opening 49.

Figure 8:
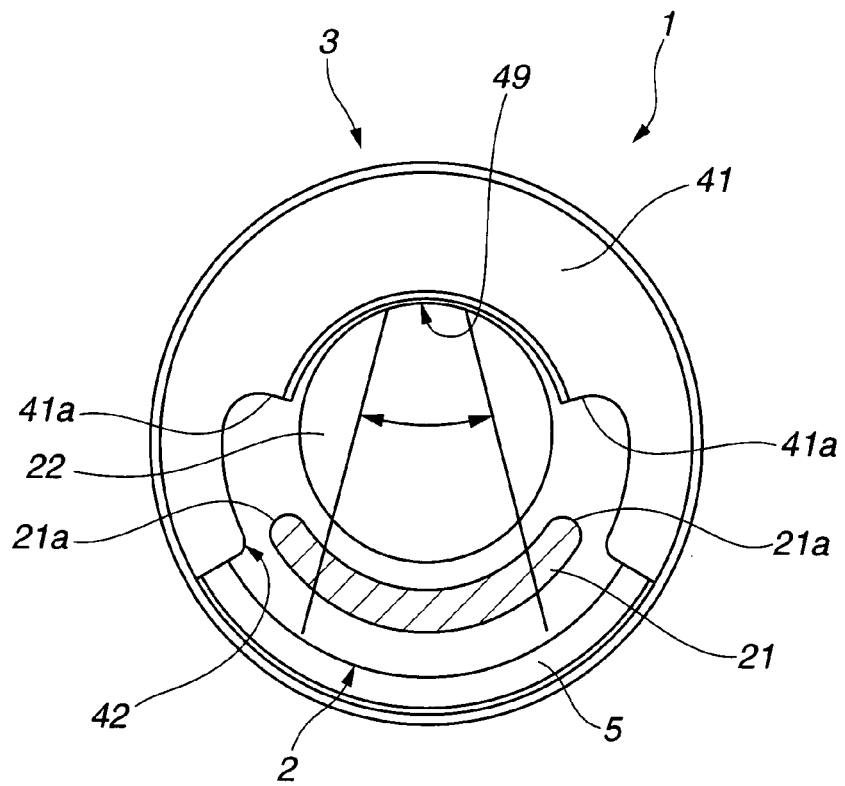

The action of the endoscope apparatus 1 comprising the endoscope cleaning sheath 3 configured as described above will now be described. First, the insertion portion 2*a* of the endoscope 2 is inserted into the endoscope hole 51 of the endoscope cleaning sheath 3. When the endoscope cleaning sheath 3 is in a state in which it is attached to the insertion portion 2*a*, the insertion portion 2*a* of the endoscope 2 is disposed as shown in FIG. 1, FIG. 2, and FIG. 8. More specifically, the light emitting end 21 shown in FIG. 1 and FIG. 8 is disposed without being blocked by the distal end surface portion 41 of the distal end configuration portion 4 comprising the endoscope cleaning sheath 3. In this disposition state, the distances from side ends 41*a* of the distal end surface portion 41 to side ends of the light emitting end 21 are substantially equidistant. Further, as shown in FIG. 2, the distal end surface 2*b* of the insertion portion 2*a* contacts against the contact surface 43 of the distal end surface portion 41.

Figure 7:
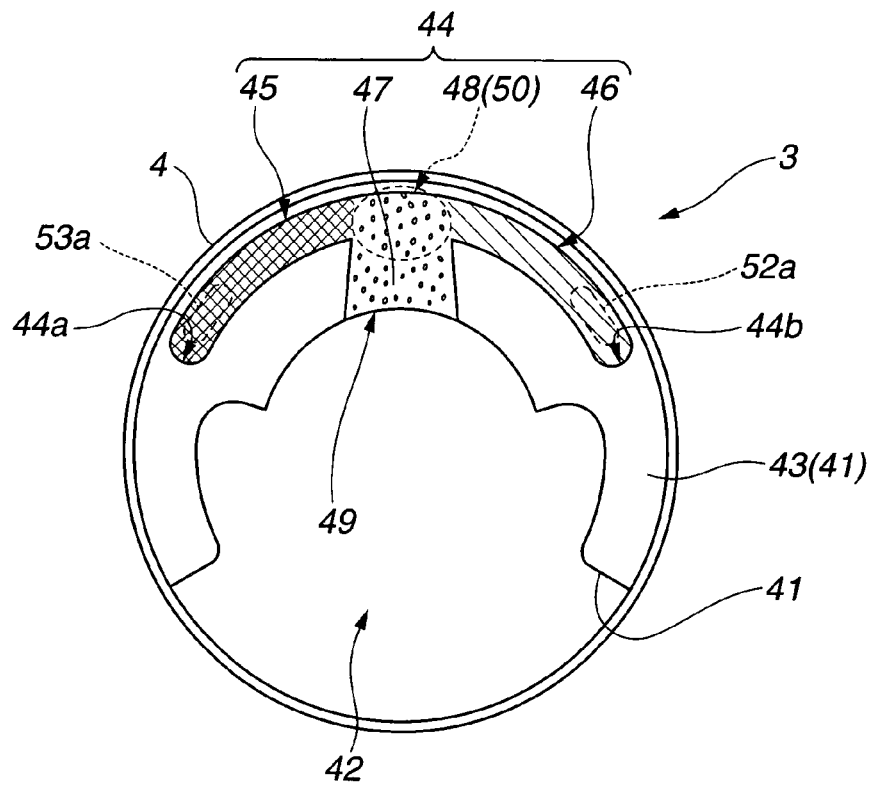

As a result, as shown in FIG. 7, the air supply distal end opening 52*a* is disposed opposing the air supply groove 46 with a predetermined positional relationship existing therebetween, and the liquid supply distal end opening 53*a* is disposed opposing the liquid supply groove 45 with a predetermined positional relationship existing therebetween. Further, the open end 44*c* is configured as the ejection opening 49 of the ejection groove 47.

Next, the distal end portion of the first air supply tube 63*a* comprising the air supply apparatus 60 is connected to the gas supply portion 6, and the distal end portion of the liquid supply tube 64 comprising the liquid supply apparatus 70 is connected to the liquid supply portion 7. Further, the signal cables 69*c*, 69*d* extending from the foot switch 69 are connected to the air supply control switch 65 and the liquid supply control switch 66, respectively.

Subsequently, in order to carry out observation inside a body cavity, the insertion portion 2*a* of the endoscope 2 to which the endoscope cleaning sheath 3 is attached is inserted into the body cavity. At this time, an illumination light that is emitted from the light emitting end 21 of the endoscope 2 illuminates the subject. The reflection light from the subject is picked up as an optical image through the observation window 22 to display an endoscopic image on the screen of a liquid crystal display so as to enable observation.

During the endoscopic observation, the air supply pump 67 and the liquid supply pump 68 are in an operating state. The valves that are respectively provided in the control switches 65 and 66 are in an initial state, i.e. a closed state. Accordingly, the air supply control switch 65 is blocking the supply of air from the second air supply tube 63*b* to the first air supply tube 63*a*. The liquid supply control switch 66 is blocking the supply of water from the liquid supply pipe 71*a* to the liquid supply tube 64.

During this kind of endoscopic observation, adhering substances such as in vivo mucus, blood, and fat adhere to the distal end surface 2*b* of the insertion portion 2*a*. As a result, a problem occurs that the illumination range of the illumination light is narrowed or that the observation field of view can not be secured due to the adhering substances. When such a problem occurs, an operator operates the first pedal 69*a* of the foot switch 69. Thereupon, the valve of the air supply control switch 65 changes from a closed state to an open state and, at the same time, the valve of the liquid supply control switch 66 changes from a closed state to an open state.

Upon the valve of the air supply control switch 65 entering an open state, air that is fed from the air supply pump 67 through the second air supply tube 63b passes through the air supply control switch 65, and thereafter is supplied to the first air supply tube 63a, the gas supply portion 6, the communicating hole 54 and the air supply hole 52. Meanwhile, upon the valve of the liquid supply control switch 66 entering an open state, the water 72 inside the liquid supply tank 71 is supplied through the liquid supply pipe 71a to pass through the liquid supply control switch 66, and thereafter is supplied to the liquid supply tube 64, the liquid supply portion 7, the communicating hole 54 and the liquid supply hole 53.

The air that has been supplied to the air supply hole 52 is supplied to the air supply groove 46 from the air supply distal end opening 52a of the air supply hole 52. Thereafter, as shown by the diagonal lines in FIG. 7, the air is supplied towards the fluid mixing portion 50. On the other hand, the water that has been supplied to the liquid supply hole 53 is supplied to the liquid supply groove 45 from the liquid supply distal end opening 53a of the liquid supply hole 53. Thereafter, as shown by the cross hatching in FIG. 7, the water is supplied towards the fluid mixing portion 50.

At the fluid mixing portion 50, the air that is supplied through the air supply groove 46 and the water that is supplied through the liquid supply groove 45 flow into each other and are mixed and changed into a fluid mixture. The fluid mixture is supplied to the ejection groove 47. The fluid mixture that is supplied to the ejection groove 47 is sprayed in a spray state towards the observation window 22, and light emitting end 21 shown in FIG. 8 from the ejection opening 49 that is the open end 44c of the ejection groove 47. At this time, the ejection range of the fluid mixture that is ejected in the spray state widens as it moves from the observation window 22 to the light emitting end 21.

Thus, adhering substances that adhere to the distal end surface 2b of the insertion portion 2a are removed by the fluid mixture in a spray state. Thereupon, the illumination range of the illumination light and the observation field of view return to their original state, and a normal endoscopic image can be obtained. Meanwhile, when the operator observes the endoscopic image and decides that removal of adhering substances that were adhered to the distal end surface 2b is complete, the operator operates the second pedal 69b of the foot switch 69. By operating the second pedal 69b, spraying of the ejection fluid at the observation window 22 and the light emitting end 21 is stopped.

Thus, the endoscope cleaning sheath comprises a tube body constituted by a multi-lumen tube including an endoscope hole, an air supply hole, and a liquid supply hole, and on a contact surface side, a distal end configuration portion comprising a liquid supply groove, an air supply groove, and an ejection groove, and provided with a T-shaped groove in which a merging portion between the liquid supply groove and the air supply groove is configured as a fluid mixing portion. As a result, for example, air as a gas that is supplied through the gas supply channel and, for example, water as a liquid that is supplied through the liquid supply channel are mixed at the fluid mixing portion that is provided in the vicinity of the ejection opening. Thereafter, the thus-mixed fluid mixture can be sprayed in a spray state from the ejection opening onto the observation window and the light emitting end of the endoscope that is disposed in the endoscope hole. Accordingly, an adhering substance that is adhered to the observation window and the light emitting end is efficiently removed by the fluid mixture in the spray state.

Further, the configuration adopted is one in which a T-shaped groove comprising a liquid supply groove, an air supply groove, a fluid ejection groove, a fluid mixing portion, and an ejection opening is formed at the contact surface side of the distal end configuration portion comprising the endoscope cleaning sheath. By adopting this configuration it is possible to reduce the number of components for obtaining a fluid mixture, and thus provide at a low cost an endoscope cleaning sheath capable of ejecting a fluid mixture in a spray state.

Figure 9:
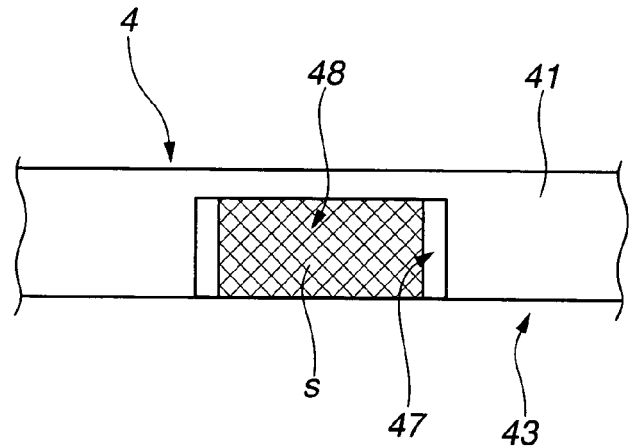

In this connection, in the endoscope cleaning sheath 3, when a spatial portion cross-sectional area of the fluid mixing portion 50 formed in the distal end surface portion 41 shown in FIG. 9 is taken as S, a cross-sectional area of the air supply hole 52 shown in FIG. 3 is taken as A, and a cross-sectional area of the liquid supply hole 53 is taken as A, the configuration is set such that the relation $$A+A \geqq S$$

is established between A and S.

As a result, air that is supplied through the air supply groove and water that is supplied through the liquid supply groove are surely mixed as a fluid mixture at the fluid mixing portion and ejected from the ejection opening in a spray state.

According to the present embodiment the insertion portion of the endoscope is configured as a flexible mirror. However, the insertion portion of the endoscope may be a rigid mirror. In that case, the endoscope in a state in which the endoscope cleaning sheath is attached is inserted into a body cavity through, for example, a trocar.

According to the present embodiment, control to eject a fluid mixture from the ejection opening 49 towards the observation window 22 and the like and control to stop the ejection is performed by operating the first pedal 69a and the second pedal 69b provided in the foot switch 69. However, the control to eject the fluid mixture towards the observation window 22 and the like from the ejection opening 49 and to stop the ejection is not limited to the above described embodiment. More specifically, the control may be of a form illustrated in FIG. 10 to FIG. 18 described hereunder, a form illustrated in FIG. 21 to FIG. 27 described hereunder, or a form illustrated in FIG. 28 to FIG. 39 described hereunder or the like.

The second embodiment of the endoscope apparatus comprising the endoscope cleaning sheath according to the present invention will now be described referring to FIG. 10 to FIG. 18.

Figure 10:
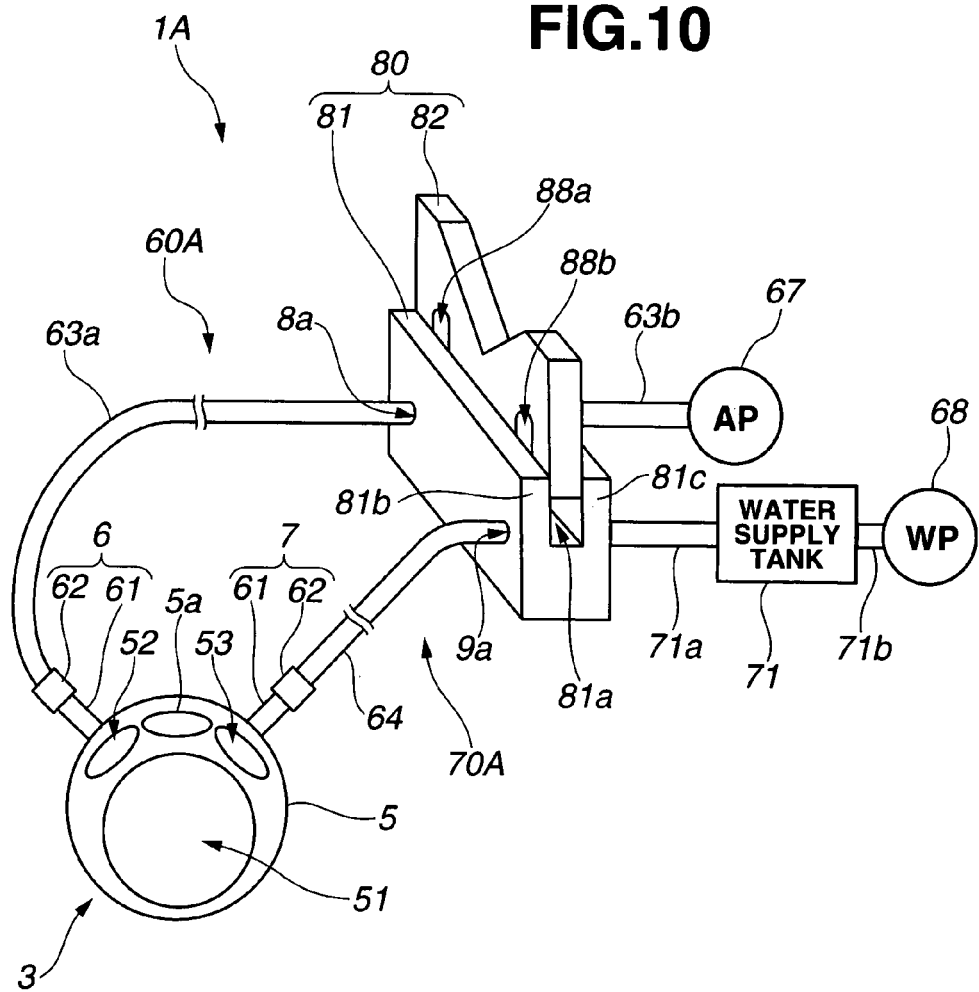
FIG. 10 to FIG. 18 are views that illustrate a second embodiment of an endoscope apparatus comprising the endoscope cleaning sheath according to the present invention.

As shown in FIG. 10, an endoscope apparatus 1A according to the present embodiment comprises an air supply apparatus 60A and a liquid supply apparatus 70A for which an ejection state changeover switch 80 is provided as a control apparatus. The ejection state changeover switch 80 is provided instead of the air supply control switch 65 comprised by the air supply apparatus 60 and the liquid supply control switch 66 comprised by the liquid supply apparatus 70 according to the first embodiment.

The ejection state changeover switch 80 mainly comprises an apparatus main unit 81 and a switch portion 82. A switch groove 81a in which the switch portion 82 is disposed is formed in the apparatus main unit 81. For this reason, an upper as shown in the figure of the apparatus main unit 81 is divided into a one-side surface portion 81b and an other-side surface portion 81c that sandwich the switch groove 81a.

Figure 11:
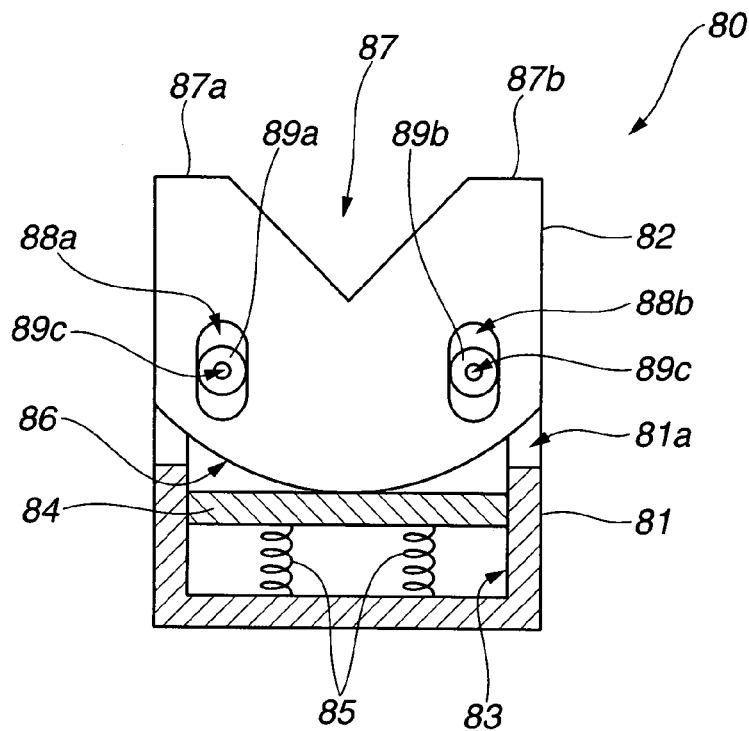

As shown in FIG. 11, a concave portion 83 is formed in the apparatus main unit 81 of the ejection state changeover switch 80. A slide member 84 and, for example, a pair of spring members 85 are provided inside the concave portion 83. The slide member 84 is disposed with respect to the concave portion 83 in a manner such that space remains therebetween to enable movement of the slide member 84 after fitting. The switch portion 82 is mounted on the top surface of the slide member 84. The spring members 85 are elastic. A plurality of the spring members 85 are disposed on the bottom surface of the concave portion 83 so as to retain the underside of the slide member 84. The spring members 85 are equipped with an energizing force that pushes the slide member 84 up as far as a predetermined height.

Consequently, when an operation is performed to press the switch portion 82 in the downward direction shown in the figure, the slide member 84 is moved downward against the energizing force of the spring members 85. In contrast, accompanying release of the operational force that presses the switch portion 82 in the downward direction shown in the figure, the slide member 84 is moved in the upward direction in the figure by the energizing force of the spring members 85.

A first main unit air supply hole 8a and a first main unit liquid supply hole 9a are provided in the one-side surface portion 81b of the apparatus main unit 81. The first main unit air supply hole 8a is a penetrating hole comprising a fluid channel, and a proximal end portion of the first air supply tube 63a is connected thereto. The first main unit liquid supply hole 9a is a penetrating hole comprising a fluid channel, and a proximal end portion of the liquid supply tube 64 is connected thereto. A second main unit air supply hole 8b and a second main unit liquid supply hole 9b are provided in the other-side surface portion 81c of the apparatus main unit 81. The second main unit air supply hole 8b is an unshown penetrating hole comprising a fluid channel, and a distal end portion of the second air supply tube 63b is connected thereto. The second main unit liquid supply hole 9b is an unshown penetrating hole comprising a fluid channel, and the distal end portion of the liquid supply pipe 71a is connected thereto. The central axis of the first main unit air supply hole 8a and the central axis of the second main unit air supply hole 8b are the same axis, and the central axis of the first main unit liquid supply hole 9a and the central axis of the second main unit liquid supply hole 9b are the same axis.

The switch portion 82 is a plate member that includes a curved portion 86 and a V-shaped groove 87. The curved portion 86 is mounted on the top surface of the slide member 84. The switch portion 82 has a pair of long holes 88a and 88b that are elongated in the vertical direction as shown in FIG. 11. The long holes 88a and 88b are formed so as to correspond with the main unit air supply holes 8a and 8b and the main unit liquid supply holes 9a and 9b. Communicating state regulation members (hereunder, referred to as "regulation members") 89a and 89b that respectively comprise a penetrating hole 89c are provided inside the long holes 88a and 88b. More specifically, an air supply regulation member 89a is disposed inside the long hole 88a corresponding to the main unit air supply holes 8a and 8b, and a liquid supply regulation member 89b is disposed inside the long hole 88b corresponding to the main unit liquid supply holes 9a and 9b. The regulation members 89a and 89b are tube bodies comprising an elastic member. Reference numeral 87a denotes a left shoulder portion and reference numeral 87b denotes a right shoulder portion, and these portions comprise a plane portion that is formed in the horizontal direction in the figure sandwiching the V-shaped groove 87.

Figure 12:
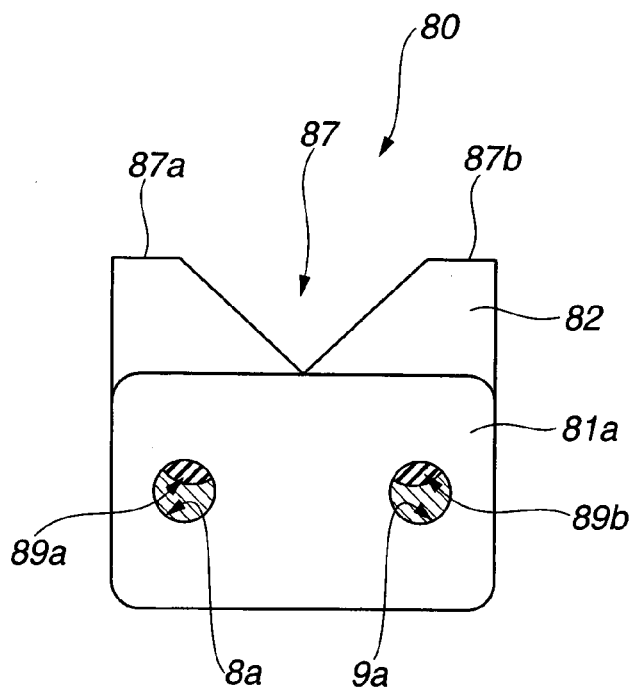
Figure 13:
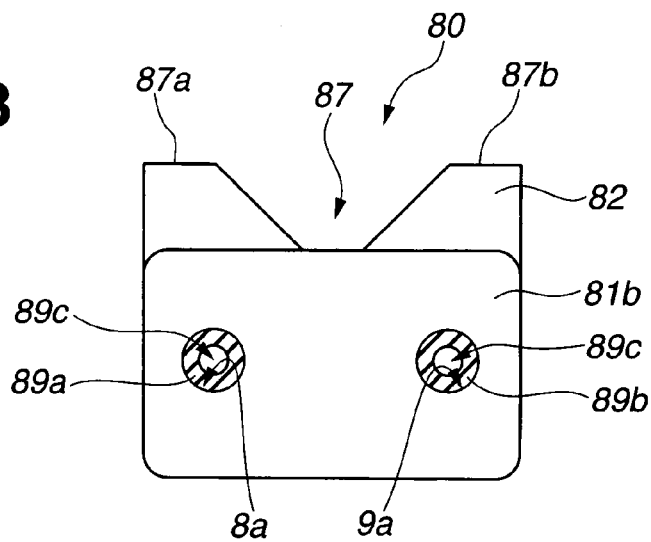
Figure 15:
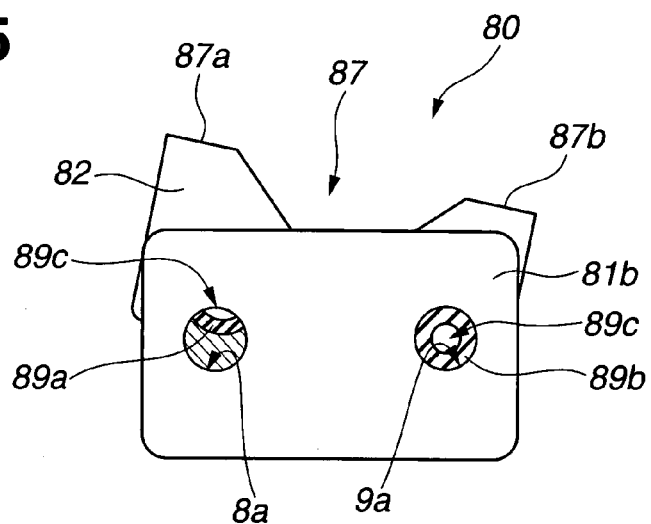
Figure 17:
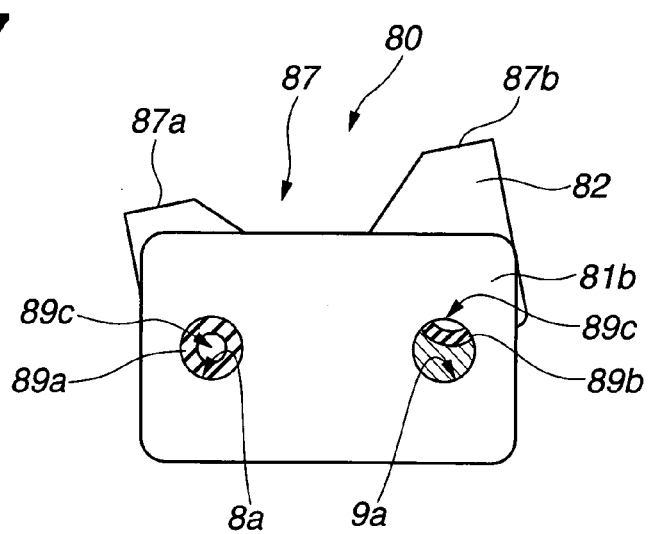

The switch portion 82 is a pushdown-type swing switch that is capable of a slide operation and a swing operation whereby the switch portion 82 inclines to one side or the other side. As a result of a slide operation of the switch portion 82, the slide member 84 is moved in the vertical direction inside the concave portion 83 as shown in FIG. 12 and FIG. 13. In a state in which the slide member 84 is pushed down, the switch portion 82 is capable of an operation whereby the switch portion 82 inclines to the right side that is one side as shown in FIG. 15 and an operation whereby the switch portion 82 inclines to the left side that is the other side as shown in FIG. 17. The configuration is such that the air supply pressure (air supply flow rate) and the liquid supply pressure (liquid supply flow rate) are changed in accordance with a pushdown operation or swing operation of the switch portion 82. This is because, in accordance with an operation of the switch portion 82, the positional relationship of the penetrating hole 89c of the air supply regulation member 89a changes with respect to the main unit air supply holes 8a and 8b, and the positional relationship of the penetrating hole 89c of the liquid supply regulation member 89b changes with respect to the main unit liquid supply hole 9a and 9b.

The remaining configuration of the endoscope apparatus 1A is the same as that of the first embodiment, and the same members are denoted by the same reference numbers and a description thereof is omitted.

The relation between the operating state of the switch portion 82 and the ejection state of a fluid mixture ejected from the ejection opening 49 will now be described referring to FIG. 12 to FIG. 18.

The ejection state changeover switch 80 shown in FIG. 12 is in the initial state. In the initial state, the switch portion 82 mounted on the slide member 84 is pushed up to a predetermined position by the energizing force of the spring members 85. More specifically, the position of the bottom of the V-shaped groove 87 of the switch portion 82 substantially matches the position of the top surface in the figure of the apparatus main unit 81. At this time, the main unit air supply holes 8a and 8b formed in the apparatus main unit 81 and the penetrating hole 89c formed in the air supply regulation member 89a are in a non-communicating state, and the main unit liquid supply holes 9a and 9b formed in the apparatus main unit 81 and the penetrating hole 89c formed in the liquid supply regulation member 89b are in a non-communicating state.

Accordingly, when the switch portion 82 of the ejection state changeover switch 80 is in the state shown in FIG. 12, the supply of air to the first air supply tube 63a from the second air supply tube 63b is blocked. Further, the supply of water from the liquid supply pipe 71a to the liquid supply tube 64 is blocked. That is, ejection of the fluid mixture from the ejection opening 49 is stopped.

The ejection state changeover switch 80 shown in FIG. 13 is in a state in which it is pushed down a predetermined amount against the energizing force of the spring members 85 of the switch portion 82, and causes the bottom of the V-shaped groove 87 to move as far as inside the apparatus main unit 81. At this time, the penetrating hole 89c of the air supply regulation member 89a and the main unit air supply holes 8a and 8b formed in the apparatus main unit 81 are in a communicating state, and the penetrating hole 89c of the liquid supply regulation member 89b and the main unit liquid supply holes 9a and 9b formed in the apparatus main unit 81 are in a communicating state. Note that, the regulation member 89a is in a state in which it is positioned in substantially the center of the long hole 88a as shown in the aforementioned FIG. 11, and the regulation member 89b is also in a state in which it is positioned in substantially the center of the long hole 88b as shown in the aforementioned FIG. 11.

When the switch portion 82 of the ejection state changeover switch 80 is in a pushed-down state as shown in FIG. 13, air is supplied to the first air supply tube 63a from the second air supply tube 63b and water is supplied from the liquid supply pipe 71a to the liquid supply tube 64. Thereafter, air that is sent from the air supply pump 67 is supplied to the air supply groove 46 through the air supply distal end opening hole 52a of the endoscope cleaning sheath 3, and water 72 that is stored in the liquid supply tank 71 is supplied to the liquid supply groove 45 through the liquid supply distal end opening 53a.

Figure 14:
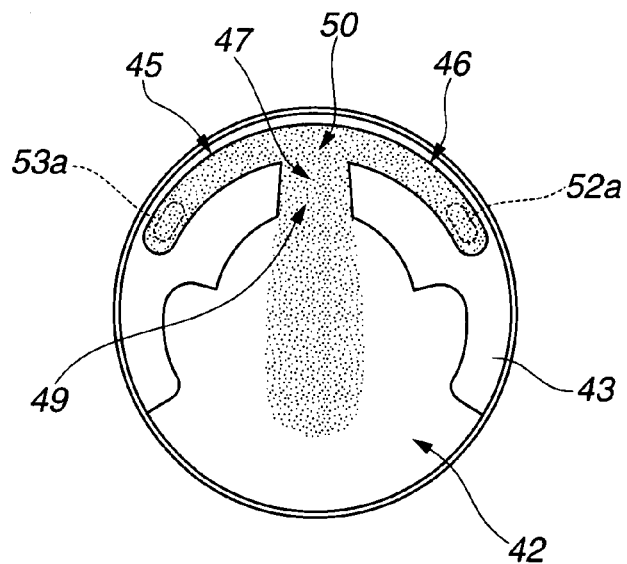

The air that is supplied through the air supply groove 46 and the water that is supplied through the liquid supply groove 45 merge at the fluid mixing portion 50 to be mixed into a fluid mixture in a spray state and supplied to the ejection groove 47. Thereupon, as shown in FIG. 14, the fluid mixture is ejected from the ejection opening 49 toward the center direction of the observation window (not shown). This ejection state is described herein as a "center ejection state."

After the switch portion 82 is placed in a pressed-down state as shown in the aforementioned FIG. 13, the ejection state changeover switch 80 shown in FIG. 15 is in a swing state in which the right shoulder portion 87b of the switch portion 82 is pushed down. At this time, the penetrating hole 89c of the air supply regulation member 89a communicates in a half-open state with the main unit air supply holes 8a and 8b formed in the apparatus main unit 81. In contrast, the penetrating hole 89c of the liquid supply regulation member 89b communicates in a fully open state in the same manner as shown in the aforementioned FIG. 13 with respect to the main unit liquid supply holes 9a and 9b formed in the apparatus main unit 81. As a result, the air supply pressure of air supplied to the first air supply tube 63a from the air supply tube 63b through the penetrating hole 89c in the half-open state is a higher pressure than the water supply pressure of water that is supplied to the liquid supply tube 64 from the liquid supply pipe 71a through the penetrating hole 89c in the fully open state.

Figure 16:
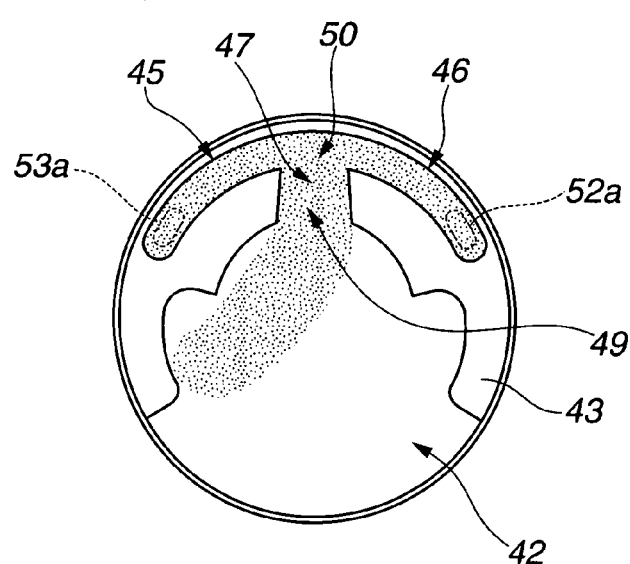

Accordingly, since the air supply pressure is higher than the water supply pressure, the fluid mixture that is ejected from the ejection opening 49 as shown in FIG. 16 curves to the side of the liquid supply distal end opening 53a to be sprayed at the left end side of the observation window (not shown) as viewed by the user.

In contrast, the ejection state changeover switch 80 shown in FIG. 17 is in a swing state in which the switch portion 82 is pushed down in the opposite direction to the state shown in the aforementioned FIG. 15 from the pushed-down state shown in FIG. 13. At this time, the penetrating hole 89c of the air supply regulation member 89a communicates in a fully open state, unlike the half-open state of the aforementioned FIG. 15, with respect to the main unit air supply holes 8a and 8b formed in the apparatus main unit 81. In contrast, the penetrating hole 89c of the liquid supply regulation member 89b communicates in a half-open state, unlike the fully open state of the aforementioned FIG. 15, with respect to the main unit liquid supply holes 9a and 9b formed in the apparatus main unit 81.

Figure 18:
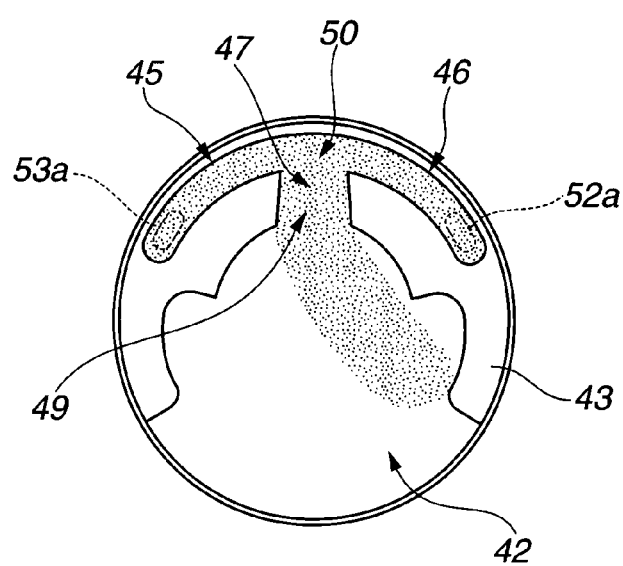

Thus, the air supply pressure of air that is supplied to the first air supply tube 63a from the air supply tube 63b through the penetrating hole 89c in a fully open state is a lower pressure than the water supply pressure of water that is supplied to the liquid supply tube 64 from the liquid supply pipe 71a through the penetrating hole 89c in a half-open state. Accordingly, since the water supply pressure is higher than the air supply pressure, the fluid mixture that is ejected from the ejection opening 49 as shown in FIG. 18 curves to the side of the air supply distal end opening 52a to be sprayed at the right end side of the observation window (not shown) as viewed by the user.

The action of the endoscope apparatus 1A configured as described above will now be described.

Similarly to the first embodiment, first the insertion portion 2a of the endoscope 2 is inserted into the endoscope hole 51 of the endoscope cleaning sheath 3. Next, the distal end portion of the first air supply tube 63a whose proximal end portion is connected to the ejection state changeover switch 80 is connected to the gas supply portion 6. Further, the distal end portion of the liquid supply tube 64 whose proximal end portion is connected to the ejection state changeover switch 80 is connected to the liquid supply portion 7. Subsequently, in order to perform observation inside a body cavity, the insertion portion 2a of the endoscope 2 having the endoscope cleaning sheath 3 attached thereto is inserted into the body cavity. At this time, the air supply pump 67 and the liquid supply pump 68 are in an operating state, and the ejection state changeover switch 80 is in the initial state shown in FIG. 12. Therefore, the supply of air to the first air supply tube 63a from the second air supply tube 63b and the supply of water to the liquid supply tube 64 from the liquid supply pipe 71a are blocked by the switch portion 82.

According to the present embodiment it is assumed that adhering substances such as in vivo mucus, blood, and fat adhere to the distal end surface 2b of the insertion portion 2a during the endoscopic observation and hinder the observation. In this case, the operator pushes down the switch portion 82 of the ejection state changeover switch 80 against the energizing force of the spring members 85 to remove the adhering substances by the two methods described hereunder.

The first method comprises pushing down the switch portion 82 by a predetermined amount against the energizing force of the spring members 85 to place the switch portion 82 in the state shown the aforementioned in FIG. 13. Thereupon, as shown in the aforementioned FIG. 14, the fluid mixture is ejected from the ejection opening 49 in a center ejection state. As a result, the fluid mixture in a spray state is sprayed against an unshown observation window or the like to remove adhering substances that are adhered to the distal end surface 2b of the insertion portion 2a so that the illumination range of the illumination light and the observation field of view return to their original favorable state.

When the operator judges that the adhering substances have been removed, the operator releases their hand from the switch portion 82. Thereupon, the switch portion 82 is pushed upward by the energizing force of the spring members 85. With that, the switch portion 82 returns to the state shown in the aforementioned FIG. 12 and ejection of the fluid mixture is stopped.

According to the second method, after the switch portion 82 is pushed down by a predetermined amount against the energizing force of the spring members 85 and placed in the state shown in the aforementioned FIG. 13, an operation is performed to repeatedly swing the switch portion 82 between the state shown in FIG. 15 and the state shown in FIG. 17. Thereupon, accompanying the swing operation of the switch portion 82, the air supply pressure of air that is supplied from the air supply pump 67 to the air supply groove 46 through the air supply hole 52 of the endoscope cleaning sheath 3 and the water supply pressure of the water 72 that is supplied to the liquid supply groove 45 through the liquid supply hole 53 change.

For this reason, after the fluid mixture that is produced by the air supplied through the air supply groove 46 and the water supplied through the liquid supply groove 45 merging at the fluid mixing portion 50 and the mixture is supplied to the ejection groove 47, the fluid mixture is ejected from the ejection opening 49. At this time, the ejection direction of the fluid mixture ejected from the ejection opening 49 changes, for example, from the direction toward the center of the observation window as shown in FIG. 14, to the direction toward the left side of the observation window as shown in FIG. 16, to once again the direction toward the center of the observation window as shown in FIG. 14, to the direction toward the right side of the observation window as shown in FIG. 18, and once again to the direction toward the center of the observation window as shown in FIG. 14 . . . and so forth, as though it were a wiper moving to remove raindrops that adhered to the windscreen of a car.

Thus, accompanying an operation that pushes down and swings the switch portion 82, the fluid mixture in a spray state is sprayed against an unshown observation window or the like while changing the ejection direction in the same manner as a wiper moves. As a result, adhering substances that adhere to the distal end surface 2b of the insertion portion 2a are removed, and the illumination range of the illumination light and the observation field of view return to their original favorable state.

Meanwhile, during observation of an endoscopic image, when the operator is concerned about a smudge caused by dirt that adheres to, for example, the right side of the screen, the operator can operate the switch portion 82 as shown in FIG. 17 to cause the fluid mixture to be ejected in the direction of the right side of the observation window to remove the dirt. After the operator judges that removal of the adhering substance is completed, the operator releases their hand from the switch portion 82. Thereby, ejection of the fluid mixture is stopped as described above.

Thus, an ejection state changeover switch is provided in the endoscope apparatus to enable swinging of a switch portion provided in the ejection state changeover switch. By causing the switch portion to swing, the positional relationship of the penetrating hole of the air supply regulation member is changed with respect to the first main unit air supply hole and the second main unit air supply hole formed in the apparatus main unit, and the positional relationship of the penetrating hole of the liquid supply regulation member is changed with respect to the first main unit liquid supply hole and the second main unit liquid supply hole formed in the apparatus main unit. As a result, the state of the penetrating hole of the air supply regulation member changes to a fully open state, a fully closed state, a half-open state and the like with respect to the first main unit air supply hole and the second main unit air supply hole. Further, the state of the penetrating hole of the liquid supply regulation member changes to a fully open state, a fully closed state, a half-open state and the like with respect to the first main unit liquid supply hole and the second main unit liquid supply hole. Accordingly, by a swing operation of the switch portion comprised by the ejection state changeover switch, the air supply pressure of gas supplied to the air supply groove and the liquid supply pressure of liquid supplied to the liquid supply groove are changed, and removal of adhering substances can thus be performed while changing the ejection direction of the fluid mixture ejected from the ejection opening.

Figure 19:
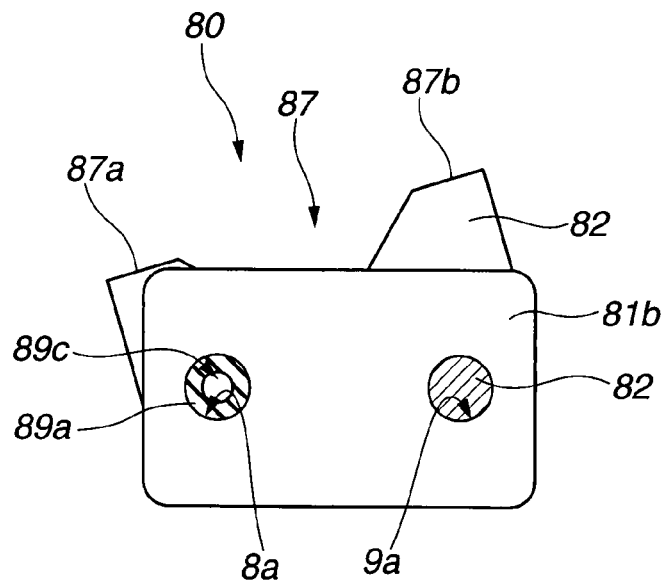
FIG. 19 is a schematic view illustrating a state of the air supply regulation member and the liquid supply regulation member when the ejection state changeover switch is in an air supply state.

The ejection state changeover switch 80 is configured to be capable of performing a swing operation so as to push the left shoulder portion 87a of the switch portion 82 further downward, as shown in FIG. 19, from the state shown in FIG. 17. As shown in FIG. 19, although the penetrating hole 89c of the air supply regulation member 89a and the main unit air supply holes 8a and 8b formed in the apparatus main unit 81 are in a communicating state, the penetrating hole 89c of the liquid supply regulation member 89b and the main unit liquid supply holes 9a and 9b formed in the apparatus main unit 81 are in a non-communicating state.

Thus, as necessary, the operator can supply only air toward the surface of the observation window 22 or the like. That is, after spraying the fluid mixture, the operator can instantly blow away water drops that adhere to the surface of the observation window 22. Therefore, immediately after cleaning, diffused reflection or the like caused by water drops that adhere to the observation window 22 is prevented and a favorable endoscopic image is obtained.

Figure 20:
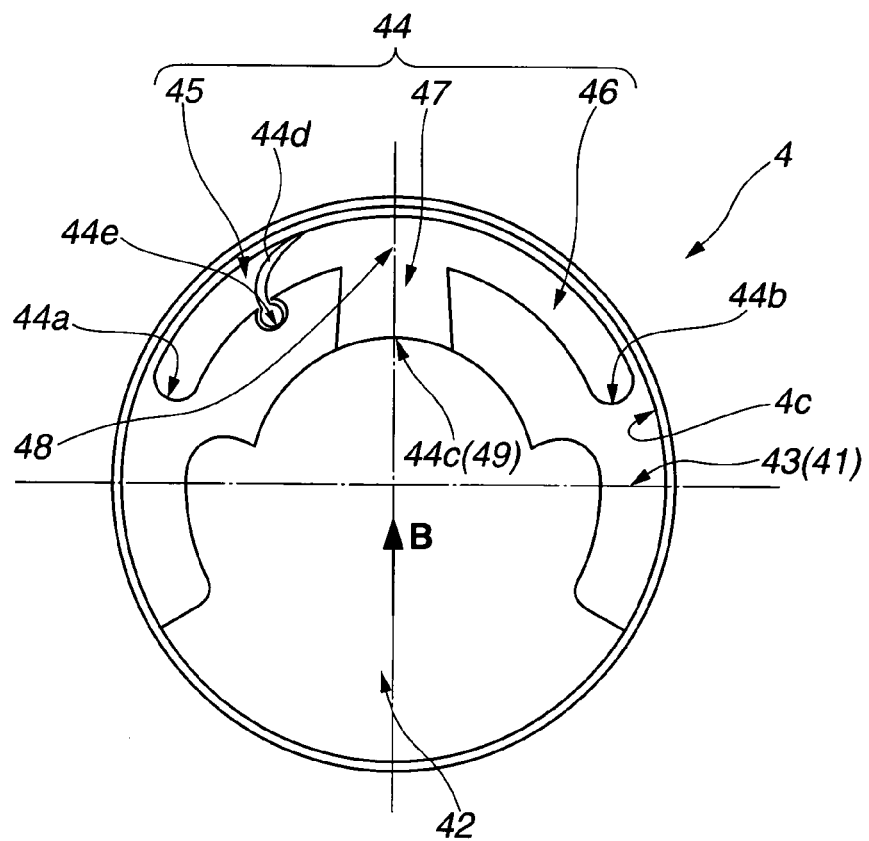
FIG. 20 is a view that illustrates the configuration of a distal end configuration portion having a valve in a liquid supply groove.

Further, as shown in FIG. 20, a valve 44d for preventing a decrease in the air supply pressure of air that is blown at the observation window 22 may be provided. The valve 44d is provided, for example, in an exchangeable condition at substantially the middle of the liquid supply groove 45, i.e. between the blocked end 44a of the liquid supply groove 45 that faces the liquid supply distal end opening 53a and the fluid merging portion 48. The valve 44d is disposed in a concave portion 44e. The valve 44d has a configuration that is normally subject to elastic deformation to a position in a blocked state by an elastic force. In a state in which liquid is supplied, the form of the valve 44d is changed by the liquid supply pressure from a blocked state to an open state. Accordingly, air that is supplied from the air supply distal end opening 52a for the purpose of supplying only air is prevented by the valve 44d from flowing into the liquid supply hole 53 through the liquid supply groove 45. Therefore, removal of water drops can be performed by ejecting air of a desired pressure toward the observation window 22 from the ejection opening 49.

According to the above described embodiment, the switch portion 82 of the ejection state changeover switch 80 is a pushdown-type swing switch. However, the switch portion 82 is not limited to a pushdown-type swing switch, and a configuration may be adopted in which the switch portion is a pushdown-type slide switch as shown in FIG. 21 to FIG. 27.

A modification example of the second embodiment in which the switch portion of the ejection state changeover switch is configured as a pushdown-type slide switch will now be described with reference to FIG. 21 to FIG. 27.

Figure 21:
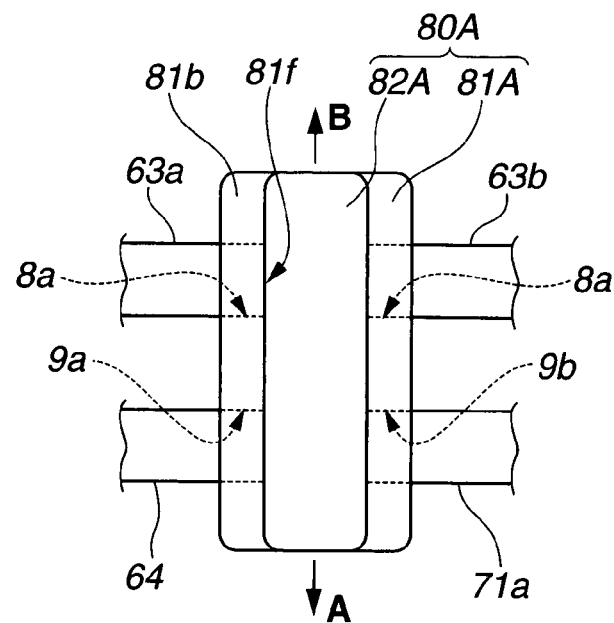
FIG. 21 to FIG. 27 are views that illustrate a modification example of the second embodiment in which a switch portion of the ejection state changeover switch is configured by a pushdown-type slide switch.
Figure 22:
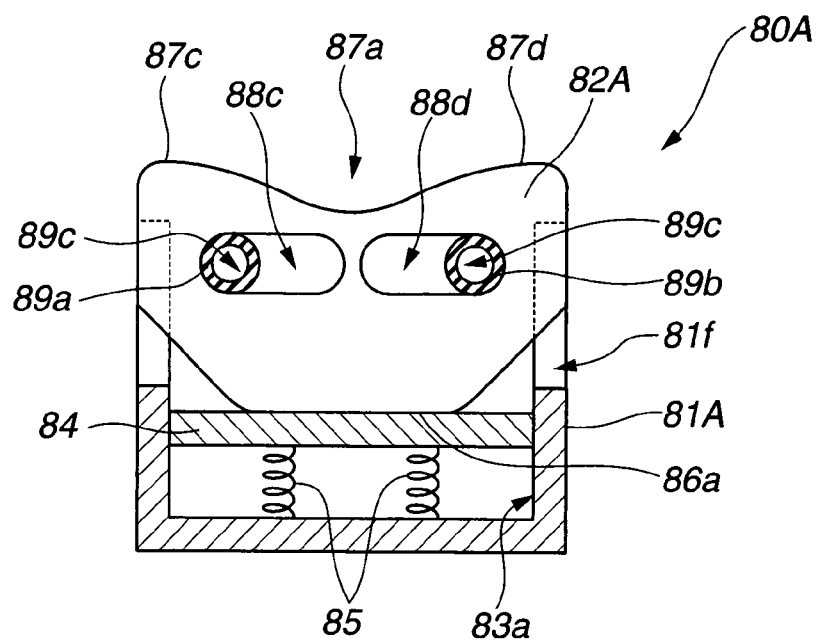

The ejection state changeover switch 80A of the present modification as shown in FIG. 21 and FIG. 22 principally comprises an apparatus main unit 81A and a switch portion 82A. The apparatus main unit 81A comprises a switch groove 81f in which the switch portion 82A is disposed. The switch portion 82A is disposed in a condition in which it is slidable in the vertical direction shown in FIG. 22 and the horizontal direction in FIG. 22 that is the direction of arrows A and B shown in FIG. 21. On the one-side surface portion 81b of the apparatus main unit 81A are provided the aforementioned first main unit air supply hole 8a and first main unit liquid supply hole 9a. On the other-side surface portion 81c of the apparatus main unit 81A are provided the aforementioned second main unit air supply hole 8b and second main unit liquid supply hole 9b.

As shown in FIG. 22, a concave portion 83a is provided in the apparatus main unit 81A of the ejection state changeover switch 80A. In the concave portion 83a are provided the slide member 84 and, for example, a plurality of the spring members 85, similarly to the above described ejection state changeover switch 80. The slide member 84 is disposed with respect to the concave portion 83a in a manner such that space remains therebetween to enable movement of the slide member 84 after fitting. The switch portion 82A is mounted on the top surface of the slide member 84. The switch portion 82A is a plate member that comprises a sliding surface portion 86a and a concave portion 87a. The sliding surface portion 86a is mounted on the top surface of the slide member 84.

A pair of long holes 88c and 88d that are elongated in the horizontal direction as shown in the figure are provided in the switch portion 82A. The long hole 88c is formed at a position corresponding to the main unit air supply holes 8a and 8b, and the long hole 88d is formed at a position corresponding to the liquid supply holes 9a and 9b. An air supply regulation member 89a comprising a penetrating hole 89c is disposed in the long hole 88c and a liquid supply regulation member 89b comprising a penetrating hole 89c is disposed in the long hole 88d. Reference numeral 87c denotes a left shoulder portion and reference numeral 87d denotes a right shoulder portion. These shoulder portions are formed in the horizontal direction in the figure in a condition sandwiching the concave groove 87a.

The switch portion 82A is a pushdown-type slide switch that is capable of a slide operation and a slide movement that moves the switch portion 82A to the arrow A side or the arrow B side. The switch portion 82A is capable of a slide operation in the state shown in FIG. 21, and moves the slide member 84 in the vertical direction between the position shown in FIG. 23 and the position shown in FIG. 24 inside the concave portion 83a. In a state in which the slide member 84 is pushed down as shown in FIG. 24, the switch portion 82A is capable of a slide movement to one side that is the arrow A side or to the other side that is arrow B side as shown in FIG. 21.

The relation between the operational state of the switch portion 82A and the ejection state of the fluid mixture that is ejected from the ejection opening 49 will now be described with reference to FIG. 21 and FIG. 23 to FIG. 27.

Figure 23:
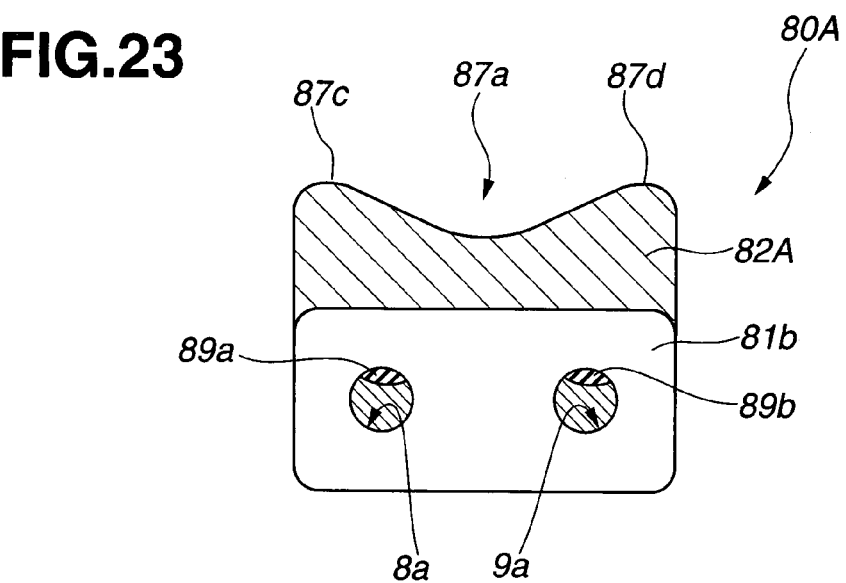
Figure 24:
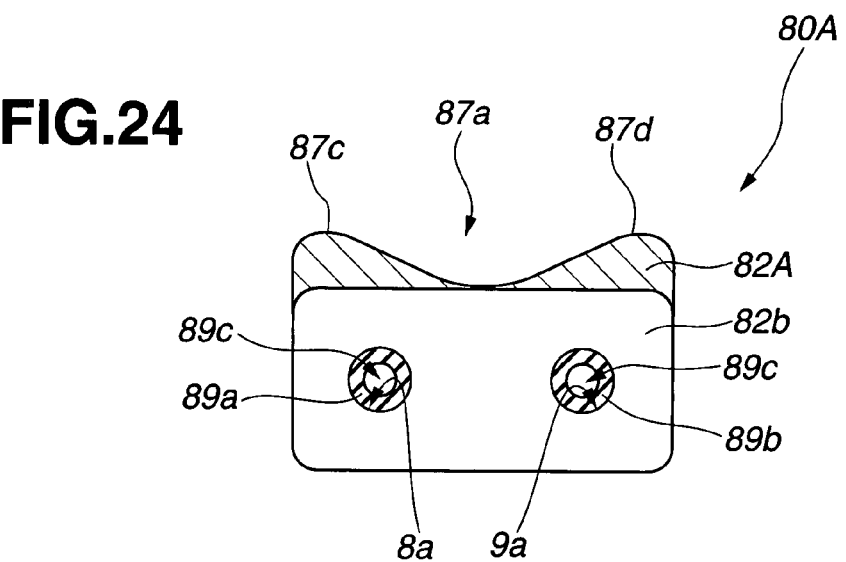

The ejection state changeover switch 80A shown in FIG. 21 and FIG. 23 is in the initial state. In the initial state the switch portion 82A is pushed up to a predetermined position by the energizing force of the spring members 85. The positions of the surfaces of the left shoulder portion 87c and the right shoulder portion 87d of the switch portion 82A substantially match the positions of the two side surfaces of the apparatus main unit 81A, without protruding from the switch groove 81f of the apparatus main unit 81A. At this time, the penetrating hole 89c of the air supply regulation member 89a and the main unit air supply holes 8a and 8b formed in the apparatus main unit 81A are in a non-communicating state, and the penetrating hole 89c of the liquid supply regulation member 89b and the main unit liquid supply holes 9a and 9b formed in the apparatus main unit 81A are in a non-communicating state.

Accordingly, when the switch portion 82A of the ejection state changeover switch 80A is in the state shown in FIG. 21, and the state shown in FIG. 23, the supply of air from the second air supply tube 63b to the first air supply tube 63a is blocked. Further, the supply of water from the liquid supply pipe 71a to the liquid supply tube 64 is blocked. More specifically, ejection of the fluid mixture from the ejection opening 49 is stopped.

The ejection state changeover switch 80A shown in FIG. 24 is in a state in which the switch portion 82A is pushed down against the energizing force of the spring members 85, and the position of the bottom of the concave portion 87c substantially matches the position of the top surface in the figure of the apparatus main unit 81A. In a state in which the positions of the surfaces of the left shoulder portion 87c and the right shoulder portion 87d of the switch portion 82A substantially match the positions of the two side surfaces of the apparatus main unit 81A as shown in FIG. 21, an operation can be performed that pushes down the switch portion 82A against the energizing force of the spring members 85. In a state in which the position of the bottom surface of the concave portion 87c substantially matches the position of the upper surface of the apparatus main unit 81A, the penetrating hole 89c of the air supply regulation member 89a communicates in a fully open state with the main unit air supply holes 8a and 8b formed in the apparatus main unit 81A, and the penetrating hole 89c of the liquid supply regulation member 89b communicates in a fully open state with the main unit liquid supply holes 9a and 9b formed in the apparatus main unit 81A. Note that, the regulation member 89a is in a state in which it is disposed at the left end with respect to the long hole 88c as shown in FIG. 22, and the regulation member 89b is in a state in which it is disposed at the right end with respect to the long hole 88d as shown in FIG. 22.

When the switch portion 82A of the ejection state changeover switch 80A is in a pushed-down state as shown in FIG. 24, air is supplied to the first air supply tube 63a from the second air supply tube 63b and water is supplied to the liquid supply tube 64 from the liquid supply pipe 71a. Thereupon, the fluid mixture enters a state in which it is ejected in the center direction from the ejection opening 49 toward the observation window as shown in the aforementioned FIG. 14.

Figure 25:
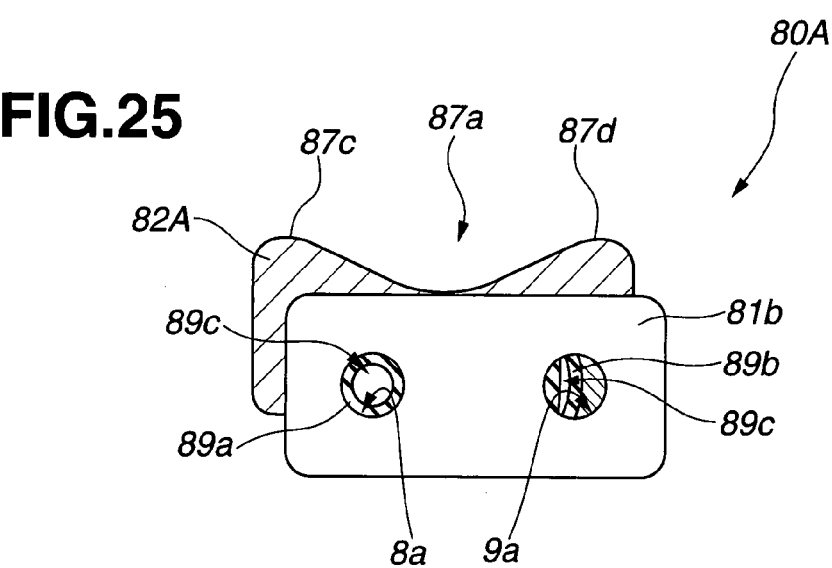

After the ejection state changeover switch 80A shown in FIG. 25 places the switch portion 82A in the pushed-down state shown in FIG. 24, the switch portion 82A is in a state in which it has been slidingly moved in the arrow B direction shown in FIG. 21. At this time, as shown by the solid line shown in FIG. 26, the left shoulder portion 87d protrudes by a predetermined amount from one side surface. In this protruding state, although the penetrating hole 89c of the air supply regulation member 89a communicates in a fully open state with the main unit air supply holes 8a and 8b that are formed in the apparatus main unit 81A in a similar manner to that shown in the aforementioned FIG. 24, the penetrating hole 89c of the liquid supply regulation member 89b communicates in a half-open state with the main unit liquid supply holes 9a and 9b formed in the apparatus main unit 81A. Consequently, the air pressure of air that is supplied to the first air supply tube 63a from the second air supply tube 63b through the penetrating hole 89c in the fully open state is a lower pressure than the water supply pressure of water that is supplied to the liquid supply tube 64 from the liquid supply pipe 71a through the penetrating hole 89c in a half-open state.

Accordingly, since the water supply pressure is higher than the air supply pressure in the fluid mixture that is ejected from the ejection opening 49 as shown in the aforementioned FIG. 18, the fluid mixture curves to the air supply distal end opening 52a side to be sprayed at the right end side of the observation window (not shown) as viewed by the user.

Figure 26:
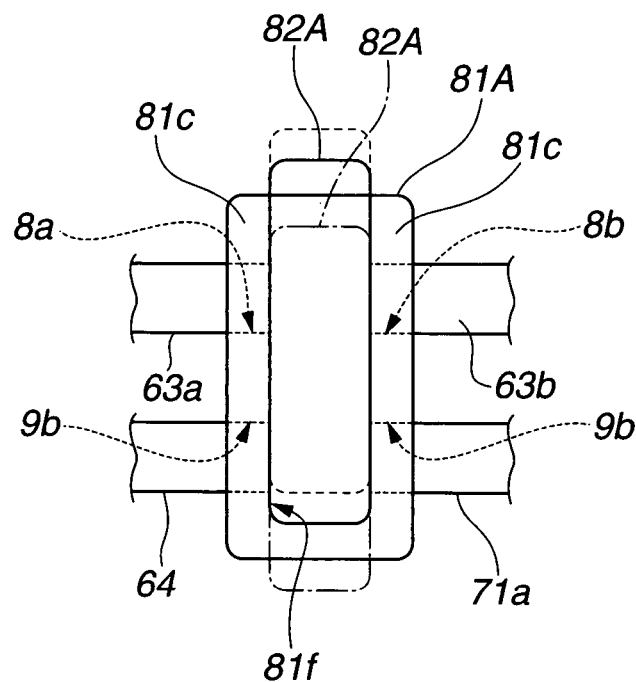
Figure 27:
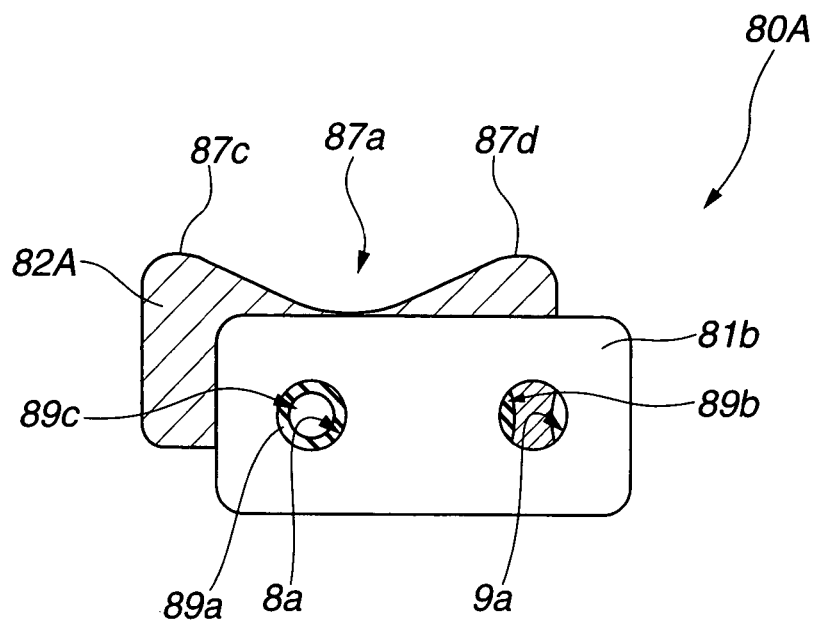

The right shoulder portion 87d of the switch portion 82 as shown in FIG. 27 is then further slidingly moved from the state shown by the solid lines in the aforementioned FIG. 26 as far as the state indicated by the broken lines in FIG. 26. Thereupon, the penetrating hole 89c of the air supply regulation member 89a and the main unit air supply holes 8a and 8b formed in the apparatus main unit 81 are placed in a communicating state and the penetrating hole 89c of the liquid supply regulation member 89b and the main unit liquid supply holes 9a and 9b formed in the apparatus main unit 81 are placed in a non-communicating state, thereby entering a state in which only air is supplied.

According to the present embodiment, the switch portion 82A is slidingly moved in the arrow A direction shown in FIG. 21 to, for example, cause the right shoulder portion 87d to protrude by a predetermined amount from the other side surface as indicated by alternate long and short dashed lines in FIG. 26. In this case, the penetrating hole 89c of the air supply regulation member 89a communicates in a half-open state with the main unit air supply holes 8a and 8b formed in the apparatus main unit 81A, while the penetrating hole 89c of the liquid supply regulation member 89b communicates in a fully open state with the main unit liquid supply holes 9a and 9b formed in the apparatus main unit 81A. As a result, the air pressure of air that is supplied to the first air supply tube 63a from the air supply tube 63b through the penetrating hole 89c that is in the half-open state is a higher pressure than the water supply pressure of water that is supplied to the water supply tube 64 from the liquid supply pipe 71a through the penetrating hole 89c in the fully open state.

Therefore, since the air supply pressure is higher than the water supply pressure in the fluid mixture that is ejected from the ejection opening 49 as shown in the aforementioned FIG. 16, the fluid mixture curves to the liquid supply distal end opening 53a side to be sprayed at the left end side of the observation window (not shown) as viewed by the user.

The endoscope apparatus comprising the ejection state changeover switch 80A configured as described above can achieve the same actions and effects as the endoscope apparatus of the second embodiment by a pushdown operation with respect to the switch portion 82A provided in the ejection state changeover switch 80A as well as a slide operation.

The third embodiment of the endoscope apparatus will now be described referring to FIG. 28 to FIG. 37.

Figure 28:
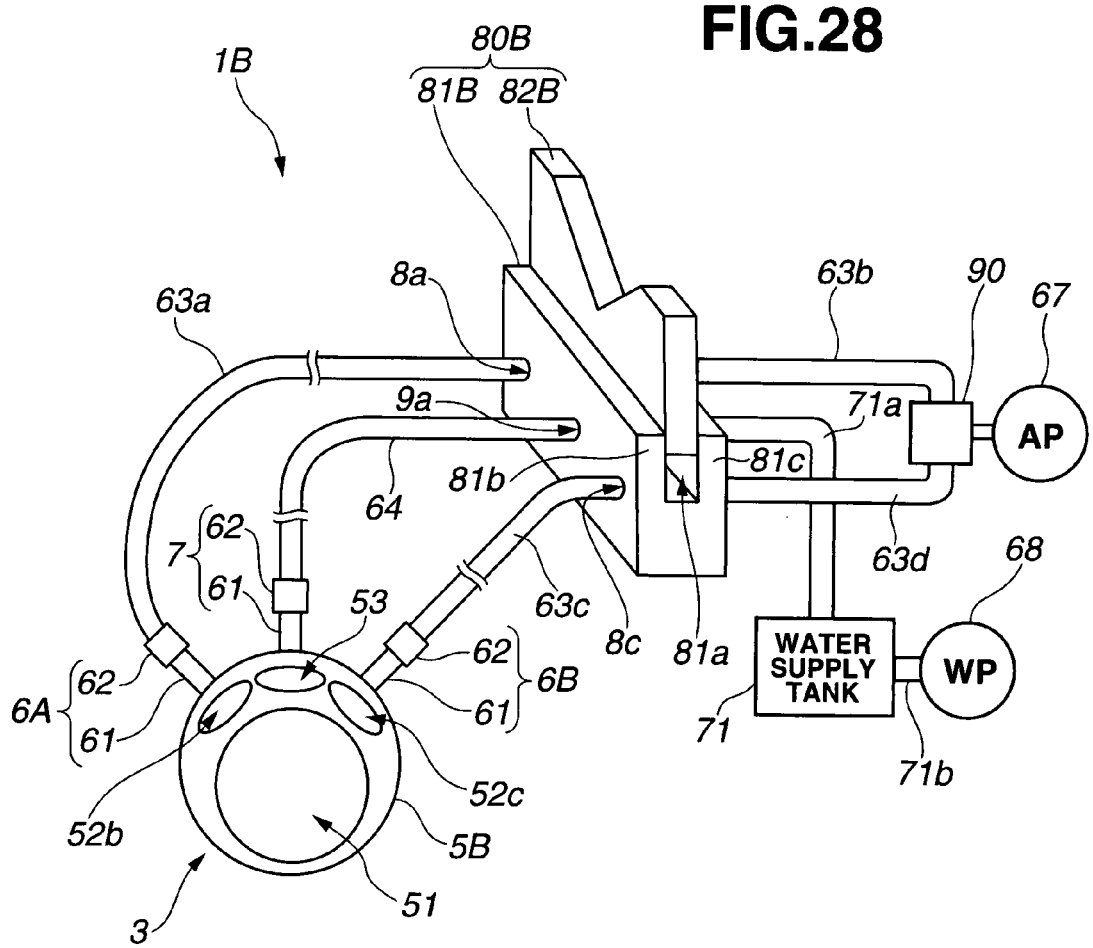
FIG. 28 to FIG. 37 are views that illustrate a third embodiment of the endoscope apparatus.

An endoscope apparatus 1B according to the present embodiment as shown in FIG. 28 comprises a tube body 5B in place of the tube body 5 of the first embodiment. It also comprises an ejection state changeover switch 80B instead of the ejection state changeover switch 80. Furthermore, according to the present embodiment, air that is supplied from the air supply pump 67 is supplied to the second air supply tube 63b and a fourth air supply tube 63d, respectively, through a branching device 90. Accordingly, the air supply apparatus 60B comprises the air supply pump 67, the branching device 90, the air supply tubes 63a, 63b, 63c and 63d, and the ejection state changeover switch 80B.

First, the configuration of the tube body 5B will be described.

Figure 33:
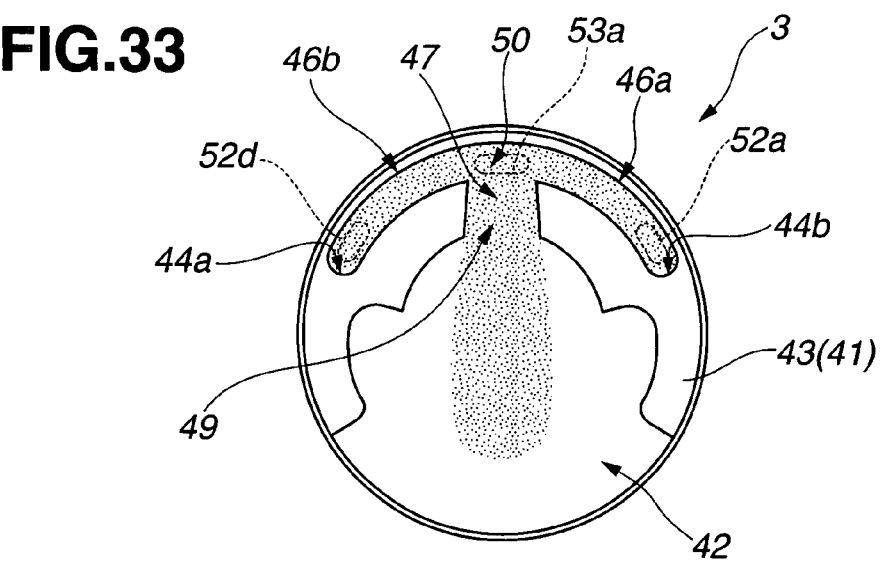

The tube body 5B comprises, for example, four holes 51, 52b, 52c, and 53. More specifically, the tube body 5B comprises a first air supply hole 52b, a second air supply hole 52c, and a liquid supply hole 53 in a thick-walled portion on the circumference of the endoscope hole 51. The holes 52b, 52c, and 53 have the same shape and the same cross-sectional area. According to the present embodiment, the first air supply hole 52b and the second air supply hole 52c are formed so to have a symmetrical positional relationship that sandwiches the vertical axis. The liquid supply hole 53 is disposed on the vertical axis at a position midway between the first air supply hole 52b and the second air supply hole 52c. In a state in which the distal end configuration portion 4 is disposed on the tube body 5B, as shown in FIG. 33 and the like, the air supply distal end opening 52a of the first air supply hole 52b is disposed facing the blocked end 44b side of the first air supply groove 46a, the air supply distal end opening 52d of the second air supply hole 52c is disposed facing the blocked end 44a side of a second air supply groove 46b, and the liquid supply distal end opening 53a of the liquid supply hole 53 is disposed facing the fluid merging portion 48. That is, according to the present embodiment, the liquid supply groove 45 according to the above-described embodiment is configured as the second air supply groove 46b.

The second pipe member 62 that comprises the first gas supply portion 6A is provided on the proximal end side of the first air supply hole 52b. The distal end portion of the first air supply tube 63a is attached to this second pipe member 62. The second pipe member 62 that comprises the second gas supply portion 6B is provided on the proximal end side of the second air supply hole 52c. The distal end portion of the third air supply tube 63c is attached to this second pipe member 62. The liquid supply portion 7 is provided on the proximal end side of the liquid supply hole 53.

Next, the configuration of the ejection state changeover switch 80B will be described. The configuration of the ejection state changeover switch 80B is, for example, substantially the same as the configuration of the ejection state changeover switch 80.

The ejection state changeover switch 80B as shown in FIG. 28 principally comprises the apparatus main unit 81B and the switch portion 82B. In the apparatus main unit 81A is formed a switch groove 81a in which the switch portion 82B is slidably disposed in the vertical direction.

The first main unit air supply hole 8a, the first main unit liquid supply hole 9a, and a third main unit air supply hole 8c are provided in the one-side surface portion 81b of the apparatus main unit 81A. The proximal end portion of the first air supply tube 63a is connected to the first main unit air supply hole 8a. The proximal end portion of the liquid supply tube 64 is connected to the first main unit liquid supply hole 9a. The proximal end portion of the third air supply tube 63c is connected to the third main unit air supply hole 8c.

Further, an unshown second main unit air supply hole 8b, second main unit liquid supply hole 9b, and fourth main unit air supply hole 8d are provided on the other-side surface portion 81c of the apparatus main unit 81A. The distal end portion of the second air supply tube 63b is connected to the second main unit air supply hole 8b. The distal end portion of the liquid supply pipe 71a is connected to the second main unit liquid supply hole 9b. The distal end portion of the fourth air supply tube 63d is connected to the fourth main unit air supply hole 8d.

The axis of the first main unit liquid supply hole 9a and the axis of the first main unit liquid supply hole 9b are the same axis. The axis of the first main unit air supply hole 8a and the axis of the second main unit air supply hole 8b, and the axis of the second main unit air supply hole 8c and the axis of the fourth main unit air supply hole 8d are the same axis. The air supply holes 8a and 8c are disposed in a condition in which they sandwich the liquid supply hole 9a.

Figure 29:
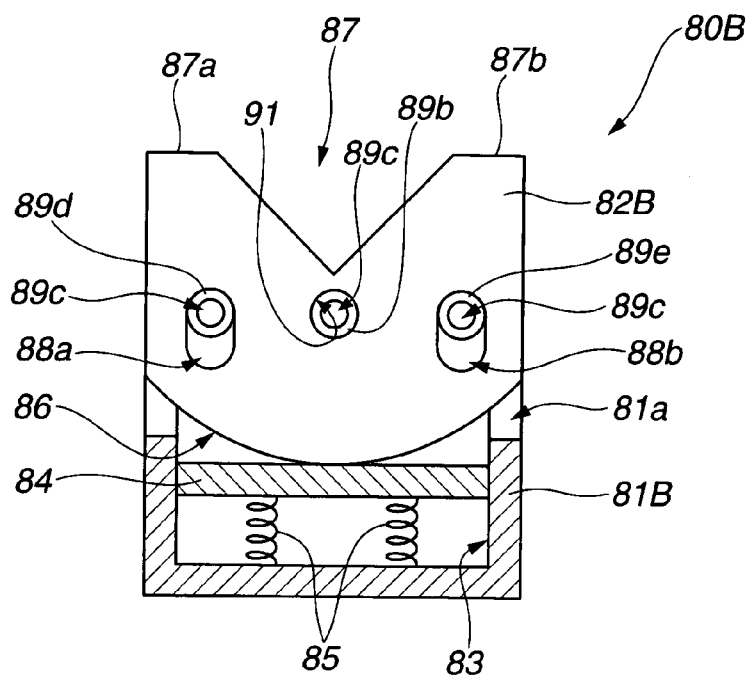

As shown in FIG. 29, the concave portion 83 is provided in the apparatus main unit 81A of the ejection state changeover switch 80B. The slide member 84 and a plurality of the spring members 85 are provided in the concave portion 83. The slide member 84 is disposed with respect to the concave portion 83 in a manner such that space remains therebetween to enable movement of the slide member 84 after fitting. The switch portion 82B is mounted on the top surface of the slide member 84.

The switch portion 82B is a plate member that includes the curved portion 86 and the V-shaped groove 87. The curved portion 86 is mounted on the top surface of the slide member 84. The switch portion 82B comprises a communicating hole 91 and long holes 88a and 88b. The communicating hole 91 corresponds in a predetermined state to the main unit liquid supply holes 9a and 9b. The liquid supply regulation member 89b is disposed in the communicating hole 91, and the long hole 88a corresponds to the main unit air supply holes 8a and 8b. A first air supply regulation member 89d is disposed inside the long hole 88a. The long hole 88b corresponds to the main unit air supply holes 8c and 8d. A second air supply regulation member 89e is disposed inside the long hole 88b. The long holes 88a and 88b are formed in a condition that sandwiches the communicating hole 91.

Figure 30:
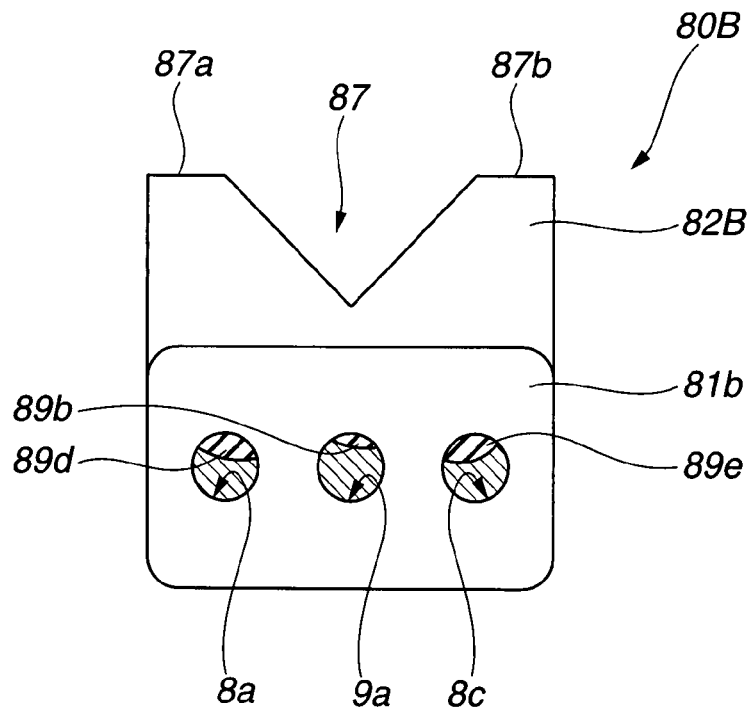
Figure 31:
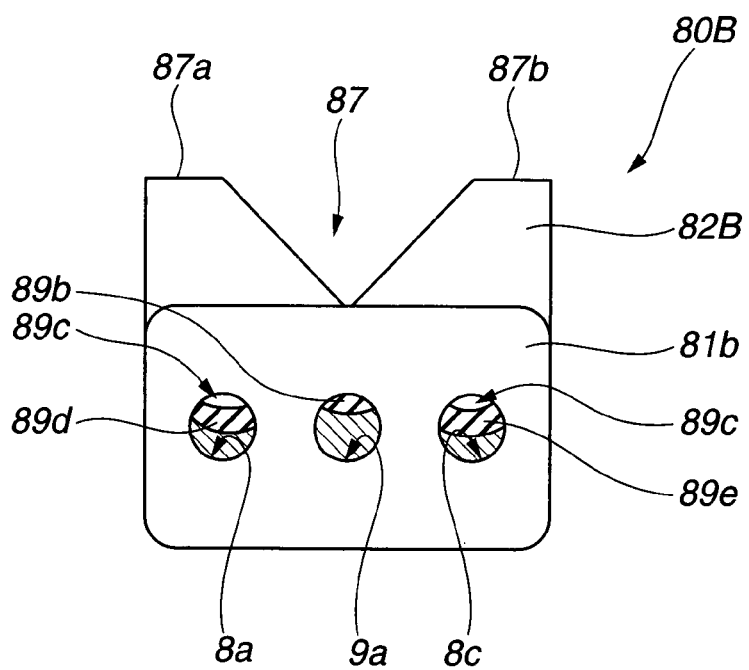
Figure 32:
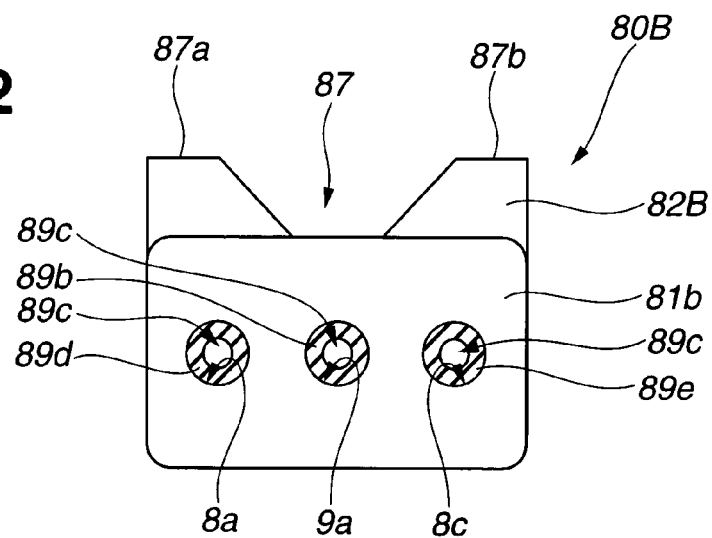
Figure 34:
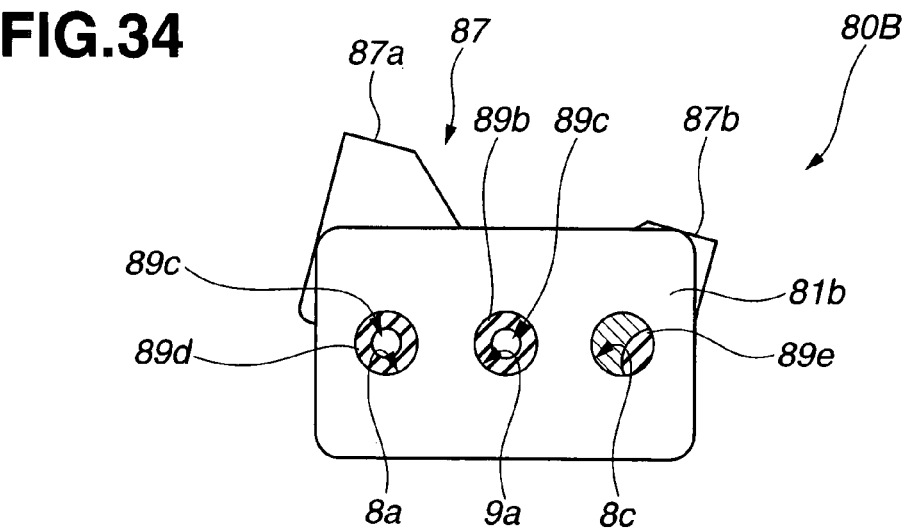
Figure 36:
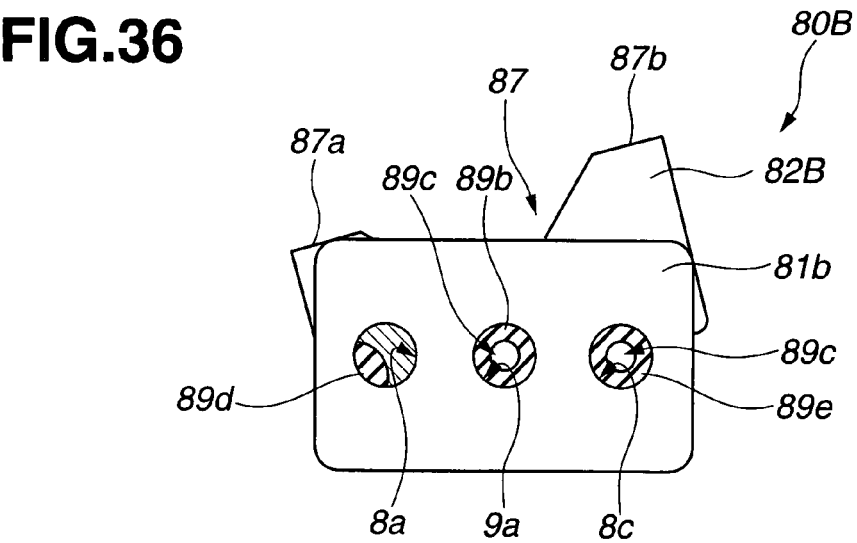

The switch portion 82B according to the present embodiment is a pushdown-type swing switch similar to that of the above described second embodiment. Accordingly, the switch portion 82B is capable of a slide operation and a swing operation. The slide operation is an operation that moves the slide member 84 in the vertical direction inside the concave portion 83, as shown in FIG. 30 to FIG. 32. The swing operation is an operation that, when the slide member 84 is in a state in which it is pushed down by a predetermined amount, inclines the slide member 84 to one side that is the right side in the figures or the other side that is the left side in the figures, as shown in FIG. 34, FIG. 36 and the like.

The remaining configuration of the endoscope apparatus 1B is the same as that of the second embodiment, and the same members are denoted by the same reference numerals and a description thereof is omitted.

The operation state of the switch portion 82B and the relation thereof with the ejection state of a fluid mixture ejected from the ejection opening 49 will now be described with reference to FIG. 30 to FIG. 37.

The ejection state changeover switch 80B shown in FIG. 30 is in the initial state. In the initial state, the switch portion 82B mounted on the slide member 84 is pushed up to a predetermined position by the energizing force of the spring members 85. More specifically, the bottom of the V-shaped groove 87 of the switch portion 82 is in a state in which it projects by a predetermined amount from the top surface in the figure of the apparatus main unit 81. At this time, the penetrating hole 89c formed in the air supply regulation member 89d and the main unit air supply holes 8a and 8b formed in the apparatus main unit 81, and the penetrating hole 89c formed in the air supply regulation member 89e and the main unit air supply holes 8c and 8d formed in the apparatus main unit 81 are in a non-communicating state. Further, the penetrating hole 89c of the liquid supply regulation member 89b and the main unit liquid supply holes 9a and 9b formed in the apparatus main unit 81 are in a non-communicating state.

Accordingly, when the switch portion 82B of the ejection state changeover switch 80B is in the state shown in FIG. 30, the supply of air to the first air supply tube 63a from the second air supply tube 63b, the supply of air to the third air supply tube 63c from the fourth air supply tube 63d, and the supply of water to the liquid supply tube 64 from the liquid supply pipe 71a are blocked. That is, ejection of the fluid mixture from the ejection opening 49 is stopped.

The ejection state changeover switch 80B shown in FIG. 31 is in a state in which it is pushed down by a predetermined amount against the energizing force of the spring members 85 of the switch portion 82B, and makes the position of the surface of the bottom of the V-shaped groove 87 of the switch portion 82 substantially match the position of the top surface in the figure of the apparatus main unit 81A. At this time, the penetrating hole 89c of the air supply regulation member 89d and the main unit air supply holes 8a and 8b formed in the apparatus main unit 81, and the penetrating hole 89c of the air supply regulation member 89e and the main unit air supply holes 8c and 8d formed in the apparatus main unit 81 communicate in a half-open state, while the penetrating hole 89c of the liquid supply regulation member 89b and the main unit liquid supply holes 9a and 9b formed in the apparatus main unit 81 are maintained in a non-communicating state.

Accordingly, the state of the switch portion 82B of the ejection state changeover switch 80B as shown in FIG. 31 is an air supply state. That is, although air is supplied to the first air supply tube 63a from the second air supply tube 63b and air is supplied to the third air supply tube 63c from the fourth air supply tube 63d, the supply of water to the liquid supply tube 64 from the liquid supply pipe 71a is blocked. Thus, only air is ejected from the ejection opening 49.

In the ejection state changeover switch 80B shown in FIG. 32, the switch portion 82B is in a state in which it is pushed down further against the energizing force of the spring members 85 from the state shown in FIG. 31. In this state, the bottom of the V-shaped groove 87 is in a state in which it is moved as far as a predetermined position inside the apparatus main unit 81A. At this time, the penetrating hole 89c of the air supply regulation member 89d and the main unit air supply holes 8a and 8b formed in the apparatus main unit 81, and the penetrating hole 89c of the air supply regulation member 89e and the main unit air supply holes 8c and 8d formed in the apparatus main unit 81 communicate in a fully open state, and the penetrating hole 89c of the liquid supply regulation member 89b and the main unit liquid supply holes 9a and 9b formed in the apparatus main unit 81 communicate in a fully open state. Note that, the regulation members 89c and 89d are in a state, as shown in FIG. 29, in which they contact against the upper end surfaces in the figure of the long holes 88a and 88b.

Accordingly, when the switch portion 82B of the ejection state changeover switch 80B is in the state shown in FIG. 32, air is supplied from the second air supply tube 63b to the first air supply tube 63a and air is supplied from the fourth air supply tube 63d to the third air supply tube 63c, and further, water is supplied from the liquid supply pipe 71a to the liquid supply tube 64. That is, as shown in FIG. 33, a fluid mixture ejected from the ejection opening 49 is ejected in a center ejection state.

The ejection state changeover switch 80B shown in FIG. 34 is in a swing state in which the right shoulder portion 87b of the switch portion 82B is pushed down from the state of the switch portion 82B shown in FIG. 32. At this time, the communicating state between the penetrating hole 89c of the air supply regulation member 89d and the main unit air supply holes 8a and 8b formed in the apparatus main unit 81 and the communicating state between the penetrating hole 89c of the liquid supply regulation member 89b and the main unit liquid supply holes 9a and 9b formed in the apparatus main unit 81 are maintained in the fully open state, while the penetrating hole 89c of the air supply regulation member 89e and the main unit air supply hole 8c and 8d formed in the apparatus main unit 81 are in a non-communicating state. As a result, air is supplied from the second air supply tube 63b to the first air supply tube 63a and water is supplied from the liquid supply pipe 71a to the liquid supply tube 64, while the supply of air from the fourth air supply tube 63d to the third air supply tube 63c is blocked.

Figure 35:
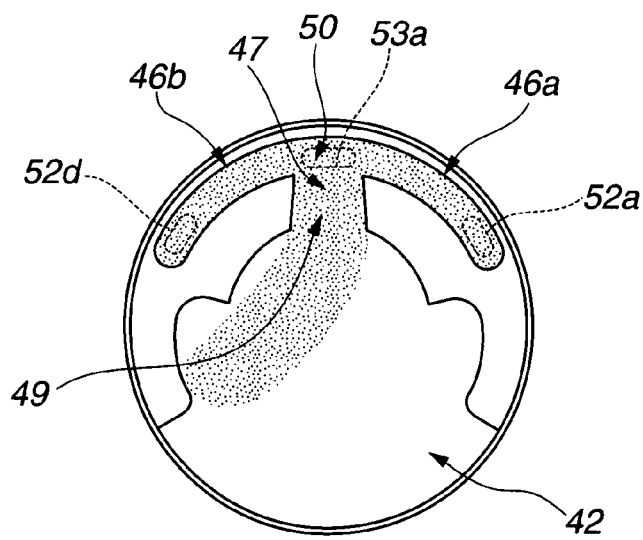

Accordingly, when the switch portion 82B of the ejection state changeover switch 80B is in the state shown in FIG. 34, as shown in FIG. 35, a fluid mixture is ejected from the ejection opening 49 towards the left side in the figure of the observation window 22.

In contrast, the ejection state changeover switch 80B shown in FIG. 36 is in a state in which the switch portion 82B has undergone a swing operation in the opposite direction to the swing state shown in the aforementioned FIG. 34. At this time, the penetrating hole 89c of the air supply regulation member 89e and the main unit air supply holes 8c and 8d formed in the apparatus main unit 81, and the penetrating hole 89c of the liquid supply regulation member 89b and the main unit liquid supply holes 9a and 9b formed in the apparatus main unit 81 communicate in a fully open state, and the penetrating hole 89c of the air supply regulation member 89d and the main unit air supply holes 8a and 8b formed in the apparatus main unit 81 are in a non-communicating state. As a result, although air is supplied from the fourth air supply tube 63d to the third air supply tube 63c, the supply of air from the second air supply tube 63b to the first air supply tube 63a is blocked. Meanwhile, water is supplied from the liquid supply pipe 71a to the liquid supply tube 64.

Figure 37:
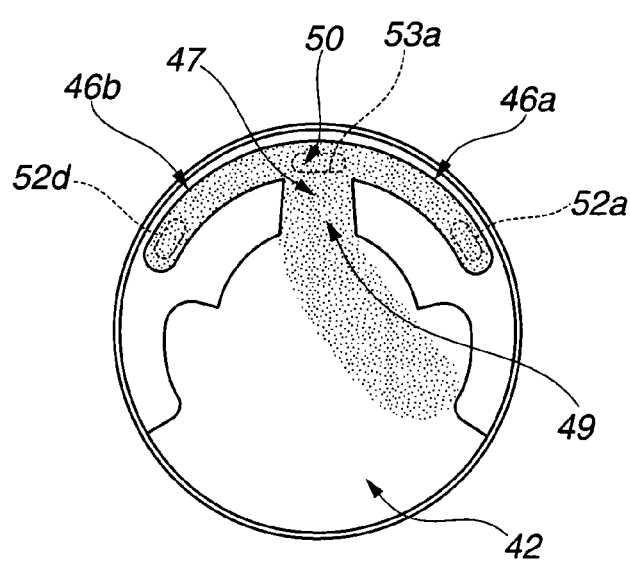

Accordingly, when the switch portion 82B of the ejection state changeover switch 80B is in the state shown in FIG. 36, as shown in FIG. 37, a fluid mixture is ejected from the ejection opening 49 towards the right side in the figure of the observation window 22.

The action of the endoscope apparatus 1B configured as described above will now be described.

Similarly to the above described first embodiment and the like, first the insertion portion 2a of the endoscope 2 is inserted into the endoscope hole 51 of the endoscope cleaning sheath 3. Next, the distal end portion of the first air supply tube 63a whose proximal end portion is connected to the ejection state changeover switch 80B is connected to the first gas supply portion 6A, and the distal end portion of the third air supply tube 63c is connected to the second gas supply portion 6B. Further, the distal end portion of the liquid supply tube 64 whose proximal end portion is connected to the ejection state changeover switch 80B is connected to the liquid supply portion 7. Subsequently, in order to perform observation inside a body cavity, the insertion portion 2a of the endoscope 2 having the endoscope cleaning sheath 3 attached thereto is inserted into the body cavity. At this time, the air supply pump 67 and the liquid supply pump 68 are in an operating state, and the ejection state changeover switch 80B is in the initial state shown in FIG. 30. Therefore, the supply of air to the first air supply tube 63a from the second air supply tube 63b and the supply of air to the third air supply tube 63c from the fourth air supply tube 63d and the supply of water to the liquid supply tube 64 from the liquid supply pipe 71a are blocked by the switch portion 82B.

According to the present embodiment it is assumed that adhering substances such as in vivo mucus, blood, and fat adhere to the distal end surface 2b of the insertion portion 2a during endoscopic observation and hinder the observation. In this case, the operator can push down the switch portion 82B of the ejection state changeover switch 80B against the energizing force of the spring members 85 to remove the adhering substances by the two methods described hereunder.

The first method comprises pushing down the switch portion 82B by a predetermined amount against the energizing force of the spring members 85 to place the switch portion 82B in the state shown in FIG. 32. Thereupon, air that is fed from the air supply pump 67 is supplied to the first air supply groove 46a through the first air supply hole 52b of the endoscope cleaning sheath 3, and is also supplied to the second air supply groove 46b through the second air supply hole 52c. Further, the water 72 that is stored in the liquid supply tank 71 is supplied to the fluid mixing portion 50 through the liquid supply hole 53. Therefore, the air that is supplied through the air supply grooves 46a and 46b and the water that is directly supplied to the fluid mixing portion 50 merge and are mixed into a fluid mixture. Thereafter, the fluid mixture is supplied to the ejection groove 47 and sprayed toward the observation window 22 in a center ejection state from the ejection opening 49 as shown in FIG. 33.

As a result, adhering substances that adhere to the distal end surface 2b of the insertion portion 2a are removed by the fluid mixture in a spray state, such that the illumination range of the illumination light and the observation field of view return to their original state. When the operator judges that the adhering substances have been removed, the operator releases the hand from the switch portion 82B. Thereupon, the switch portion 82B is pushed upward by the energizing force of the spring members 85 to return to the state shown in FIG. 30. Thus, ejection of the fluid mixture towards the observation window 22 and the light emitting end 21 is stopped.

According to the second method, after the switch portion 82B is pushed down by a predetermined amount against the energizing force of the spring members 85, a swing operation is performed that repeatedly swings the switch portion 82B between the state shown in the aforementioned FIG. 34 and the state shown in FIG. 36. Thereupon, in a state in which the water 72 stored in the liquid supply tank 71 is being supplied to the liquid supply hole 53, the air supply state changes to the first air supply hole 52b or the second air supply hole 52c of the endoscope cleaning sheath 3 from the air supply pump 67. That is, accompanying the swing operation of the switch portion 82B, for example, the air pressure gradually changes from a state in which air is being supplied only to the first air supply hole 52b to a state in which air is supplied only to the second air supply hole 52c, and the air pressure then gradually changes from the state in which air is being supplied only to the second air supply hole 52c to a state in which air is supplied only to the first air supply hole 52b.

For example, in a state in which air is supplied only through the first air supply groove 46a and water is supplied directly to the fluid mixing portion 50 such that the fluid mixture is ejected to the left end side as shown in FIG. 35, the operator starts an operation to swing the switch portion 82B. Thereupon, accompanying swinging of the switch portion 82B, the supply of air to the second air supply groove 46b is started and after passing through a state in which the air pressure of the air that is being supplied to the first air supply groove 46a gradually decreases, the water that is directly supplied to the fluid mixing portion 50 changes to a center ejection state as shown in FIG. 33. Thereafter, as the swing operation of the switch portion 82B is continued, a state is passed through in which the air pressure supplied to the second air supply groove 46b exceeds the air pressure supplied to the first air supply groove 46a, and thus the water that is directly supplied to the fluid mixing portion 50 changes to a state in which it is ejected to the right end side as shown in FIG. 37. More specifically, accompanying the swing operation of the switch portion 82B, the ejection direction of the fluid mixture changes in the same manner as a car wiper operates when removing raindrops that attach to the windscreen of a car.

As a result, adhering substances that attached to the distal end surface 2b of the insertion portion 2a can be removed by a fluid mixture in a spray state for which the ejection direction is changed in the same manner as the movement of a windscreen wiper accompanying a swing operation of the switch portion 82B.

Thus, by taking into consideration the number and positions of air supply holes and liquid supply holes provided in a tube body when performing suitable control with a control apparatus of fluids supplied to the respective air supply holes and liquid supply holes, the ejection direction of a fluid mixture that is ejected from an ejection opening can be changed to remove adhering substances.

Figure 38:
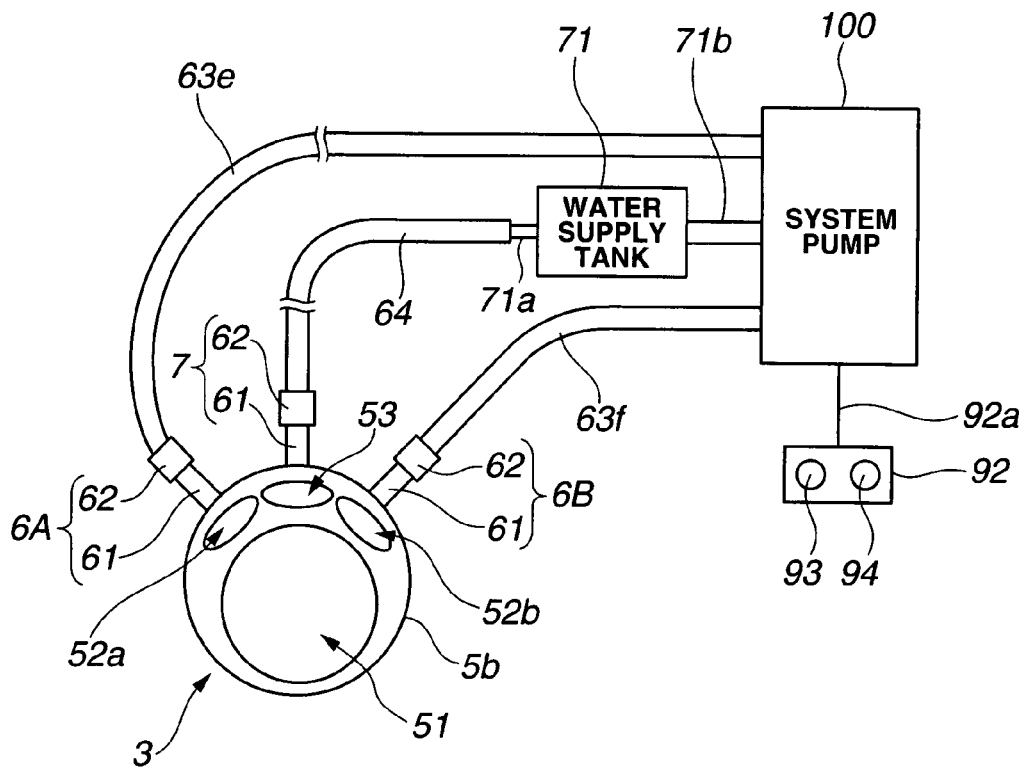
FIG. 38 is a view that illustrates the configuration of an endoscope apparatus comprising a system pump.
Figure 39:
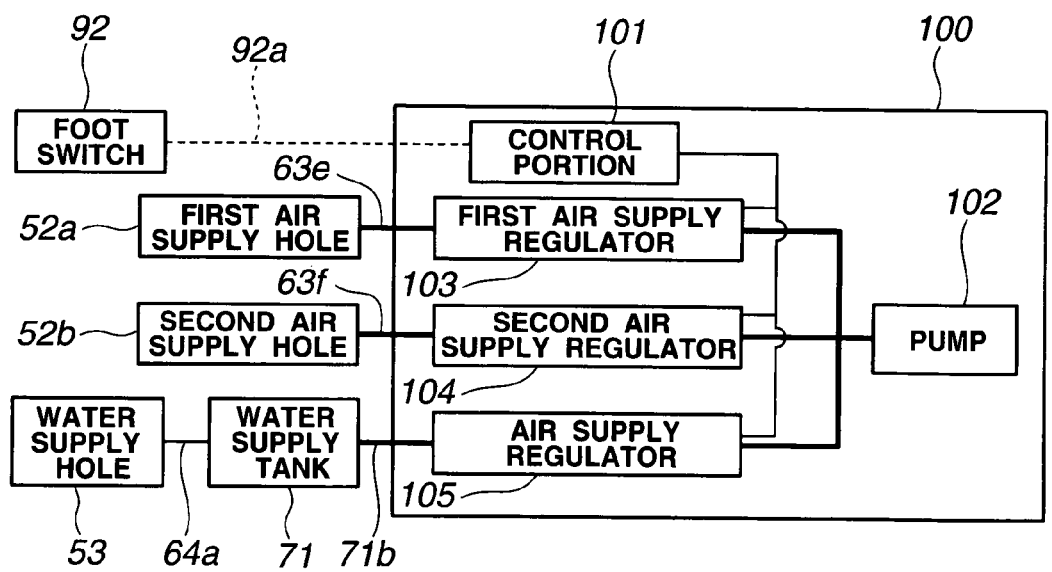
FIG. 39 is a block diagram that illustrates the configuration and action of the system pump.

In the above described embodiments, the ejection direction of a fluid mixture that is ejected from an ejection opening is changed by providing an ejection state changeover switch having a manually operated switch portion as a control apparatus. However, a control apparatus that suitably changes the ejection direction of a fluid mixture ejected from an ejection opening is not limited to an ejection state changeover switch having a manual switch portion. More specifically, a configuration may be adopted, for example as shown in FIG. 38, in which a system pump is provided as a control apparatus. In the system pump, the fluid pressure of fluids that are respectively supplied, for example, to the first air supply hole 52b, the second air supply hole 52c, and the liquid supply hole 53 is changed using regulators that correspond to each fluid channel as shown in FIG. 39.

The configuration and action of an endoscope apparatus comprising a system pump as a control apparatus will now be described with reference to FIG. 38 and FIG. 39.

As shown in FIG. 38, an endoscope apparatus 1C comprises a system pump apparatus 100. The system pump apparatus 100 is provided with a foot switch 92 as an operation instruction switch. The foot switch 92 comprises a first pedal 93 and a second pedal 94. By performing an ON operation for the first pedal 93, the fluid mixture ejected from the ejection opening 49 carries out removal of adhering substances in a center ejection state. In contrast, by performing an ON operation for the second pedal 94, the fluid mixture ejected from the ejection opening 49 carries out removal of adhering substances while changing the ejection direction.

Note that, in the present embodiment, instead of the first air supply tube 63a, the distal end portion of a fifth air supply tube 63e is connected to the second pipe member 62 of the first gas supply portion 6A. Further, instead of the third air supply tube 63c, the distal end portion of a sixth air supply tube 63f is connected to the second pipe member 62 of the second gas supply portion 6B. The proximal end portions of the air supply tubes 63e and 63f are connected to the system pump. Further, the distal end portion of the liquid supply tube 64 is connected to the second pipe member 62 of the liquid supply portion 7, and the proximal end portion of the liquid supply tube 64 is connected to the liquid supply pipe 71a of the water supply tank 71. Note that, the operation instruction switch is not limited to a foot switch, and may be a push button switch or the like that is provided to the operation portion of the endoscope. Reference numeral 92a denotes a signal cable. The remaining configuration is the same as that of the third embodiment, and the same members are denoted by the same reference numbers and a description thereof is omitted.

As shown in FIG. 39, the system pump apparatus 100 principally comprises a control portion 101, a pump 102, a first air supply regulator 103, a second air supply regulator 104, and a water supply regulator 105. The pump 102 is connected to the respective regulators 103, 104, and 105 through tube members and a branching device.

The pump 102 is driven/stopped under the operation of a main switch (not shown) provided in the system pump apparatus 100. The control portion 101 sets the output state of the respective regulators 103, 104, and 105 on the basis of a previously registered program. More specifically, the control portion 101 controls the air pressure of air that is supplied to the fifth air supply tube 63e, the air pressure of air that is supplied to the sixth air supply tube 63f, and the water supply pressure of water supplied to the liquid supply tube 64. The foot switch 92 is electrically connected to the control portion 101.

The action of the system pump apparatus 100 will now be described.

The action when the operator performs an ON operation for the first pedal 93 of the foot switch 92 will be described.

The operator performs an ON operation for the first pedal 93 of the foot switch 92 when the pump 102 is in an operating state. Thereupon, a first instruction signal that instructs the removal of adhering substances using a center ejection state is outputted to the control portion 101 from the foot switch 92. Upon receiving the first instruction signal, in order to achieve the ejection state shown in the aforementioned FIG. 33, i.e. to achieve a fluid supply state caused by the operation state of the switch portion 82B shown in FIG. 32, the control portion 101 outputs a control signal to each of the regulators 103, 104, and 105. Air of, for example, a pressure A is then supplied to the fifth air supply tube 63e through the regulator 103 from the pump 102. Air of, for example, the pressure A is also supplied to the sixth air supply tube 63f through the regulator 104 from the pump 102. Further, air for supplying water of the pressure A to the water supply tube 64 is supplied to the pressurized pipe 71b through the regulator 104 from the pump 102.

Consequently, air at the pressure A is supplied to the first air supply hole 52b and the second air supply hole 52c and water at the pressure A is supplied to the liquid supply hole 53, such that removal of adhering substances is performed by ejecting a fluid mixture in a center ejection state from the ejection opening 49 as shown in the aforementioned FIG. 33.

In contrast, when the operator performs an ON operation for the second pedal 94 of the foot switch 92 when the pump 102 is in an operating state, a second instruction signal that instructs the removal of adhering substances by changing the ejection direction of the fluid mixture is output to the control portion 101 from the foot switch 92. Upon receiving the second instruction signal, the control portion 101 outputs a control signal that is based on a previously registered program to each of the regulators 103, 104, and 105. For example, air is supplied from the pump 102 to the fifth air supply tube 63e through the regulator 103 in the order of air supply pressure A, air supply pressure B, air supply pressure A, air supply pressure C, and air supply pressure A, for example, at intervals of a time t1. Further, air is supplied from the pump 102 to the sixth air supply tube 63f through the regulator 104 in the order of air supply pressure A, air supply pressure C, air supply pressure A, air supply pressure B, and air supply pressure A, for example, at intervals of the time t1. Meanwhile, air for supplying water at the pressure A to the water supply tube 64 is supplied to the pressurized pipe 71b from the pump 102 through the regulator 104.

Thus, by changing the pressure of air that is supplied to the first air supply hole 52b and the pressure of air that is supplied to the second air supply hole 52c at intervals of the time t1, the ejection direction of the fluid mixture that is ejected from the ejection opening 49 changes from the center ejection state shown in FIG. 33, to the ejection state shown in FIG. 35, to the center ejection state shown in FIG. 33, to the ejection state shown in FIG. 37, and back to the center ejection state shown in FIG. 33, to thereby perform removal of adhering substances in the same manner as the movement of a wiper that removes raindrops that adhere to the windscreen of a car.

Therefore, by employing a system pump as the control apparatus of the endoscope apparatus, the fluid mixture is placed in a center ejection state to remove adhering substances without the operator performing a hand operation on the switch portion. Further, the ejection direction of the fluid mixture can be changed in the same manner as a wiper to remove adhering substances.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope cleaning sheath, comprising:
   a tube body including an endoscope disposition hole into which is inserted and disposed an elongated insertion portion of an endoscope provided with at least an observation window at a distal end surface of the insertion portion, at least one liquid supply hole configuring a liquid supply channel that supplies a liquid such as water, and at least one gas supply hole configuring a gas supply channel that supplies a gas such as air; and a distal end configuration portion that is a cylindrical body provided in a fixed condition at a distal end portion of the tube body, in a state in which an inner surface of a distal end surface of the tube body and a distal end surface of the insertion portion of the endoscope contact against each other at a contact surface at which a part of the inner surface of the distal end surface of the tube body and a part of the distal end surface of the insertion portion of the endoscope contact against each other, that is the inner surface of a distal end portion including a notch portion that places in an exposure state the observation window provided on the distal end surface of the endoscope that is inserted and disposed in the endoscope disposition hole, the distal end configuration portion having a fluid mixing portion that causes a liquid that is supplied through the liquid supply hole and a gas that is supplied through the gas supply hole to merge to thereby mix a liquid and a gas, and a concave portion configuring an ejection opening that ejects a fluid mixture that is mixed at the fluid mixing portion towards the observation window of the endoscope, wherein the concave portion including a liquid supply groove configuring a fluid channel in which one end that is formed along an inner circumferential surface of the distal end configuration portion is closed, and that supplies a liquid that is supplied through a distal end side opening of the liquid supply hole that is disposed on the end side that is closed to the fluid mixing portion to which the other end leads and a gas supply groove configuring a fluid channel in which one end that is formed along an inner circumferential surface of the distal end configuration portion is closed, and that supplies a gas that is supplied through a distal end side opening of the gas supply hole that is disposed on the end side that is closed to the fluid mixing portion to which the other end leads.

2. The endoscope cleaning sheath according to claim 1, wherein the tube body is a multi-lumen tube having the endoscope disposition hole, the liquid supply hole and the gas supply hole.

3. The endoscope cleaning sheath according to claim 1, wherein, in a configuration in which the tube body includes one liquid supply hole and one gas supply hole, the concave portion is a T-shaped groove, the T-shaped groove including:
a fluid mixture supply groove configuring a fluid channel which is provided in the direction of a central axis of the endoscope disposition hole from a fluid merging portion configuring a fluid mixing portion at which a gas that is supplied through the gas supply groove and a liquid that is supplied through the liquid supply groove merge.

4. The endoscope cleaning sheath according to claim 1, wherein, in a configuration in which the tube body includes one liquid supply hole and two gas supply holes that sandwich the liquid supply hole, the concave portion is a T-shaped groove, the T-shaped groove including:

a first gas supply groove configuring a fluid channel in which one end that is formed along an outer circumferential surface of the distal end configuration portion is closed, and that supplies a gas that is supplied through a distal end side opening of one of the gas supply holes that is disposed on the end side that is closed to the fluid mixing portion to which the other end leads;

a second gas supply groove configuring a fluid channel in which one end that is formed along an outer circumferential surface of the distal end configuration portion is closed, and that supplies a gas that is supplied through a distal end side opening of the other of the gas supply holes that is disposed on the end side that is closed to the fluid mixing portion to which the other end leads;

a fluid mixture supply groove with respect to which a distal end side opening of the liquid supply hole disposed in an opposing condition, and which configures a fluid channel that is provided in the direction of a central axis of the endoscope disposition hole from a fluid merging portion configuring a fluid mixing portion at which a liquid that is supplied through the liquid supply hole, a gas that is supplied through the first gas supply groove, and a gas that is supplied through the second gas supply groove merge.

* * * * *